United States Patent
Mabray et al.

(10) Patent No.: US 10,828,414 B2
(45) Date of Patent: Nov. 10, 2020

(54) MAGNETIC FILTRATION DEVICES AND METHODS RELATED THERETO

(71) Applicant: The Regents of the University of California, Oakland, CA (US)

(72) Inventors: Marc C. Mabray, San Francisco, CA (US); Steven W. Hetts, Hillsborough, CA (US); Prasheel V. Lillaney, San Francisco, CA (US); Aaron D. Losey, San Francisco, CA (US); Caroline D. Jordan, San Francisco, CA (US); Sravani Kondapavulur, San Jose, CA (US); Andre M. Cote, Daly City, CA (US)

(73) Assignee: The Regents of the University of California, Oakland, CA (US)

( * ) Notice: Subject to any disclaimer, the term of this patent is extended or adjusted under 35 U.S.C. 154(b) by 539 days.

(21) Appl. No.: 15/551,245

(22) PCT Filed: Feb. 17, 2016

(86) PCT No.: PCT/US2016/018314
§ 371 (c)(1),
(2) Date: Aug. 15, 2017

(87) PCT Pub. No.: WO2016/134047
PCT Pub. Date: Aug. 25, 2016

(65) Prior Publication Data
US 2018/0043083 A1     Feb. 15, 2018

Related U.S. Application Data
(60) Provisional application No. 62/193,503, filed on Jul. 16, 2015, provisional application No. 62/117,322, filed on Feb. 17, 2015.

(51) Int. Cl.
A61M 1/36 (2006.01)
A61F 2/01 (2006.01)
(Continued)

(52) U.S. Cl.
CPC ............. *A61M 1/3618* (2014.02); *A61F 2/01* (2013.01); *A61K 31/704* (2013.01); *A61K 41/00* (2013.01);
(Continued)

(58) Field of Classification Search
CPC .................. A61F 2/01; A61M 1/3618; A61M 2202/0014; A61M 2202/0071; A61M 2202/20; A61N 2/00
See application file for complete search history.

(56) References Cited

U.S. PATENT DOCUMENTS

| | | | |
|---|---|---|---|
| 2,985,792 A | 5/1961 | Bates et al. | |
| 5,186,827 A * | 2/1993 | Liberti | A23L 3/32 210/222 |

(Continued)

FOREIGN PATENT DOCUMENTS

| | | |
|---|---|---|
| CN | 103182086 | 7/2013 |
| WO | 2007049286 | 5/2007 |
| WO | 2014100201 | 6/2014 |

OTHER PUBLICATIONS

Crouse et al. (2008) "Regent control over the size, uniformity, and composition of Co—Fe—O nanoparticles" Journal of Materials Chemistry,18: 4146-4153.

*Primary Examiner* — Benjamin J Klein
(74) *Attorney, Agent, or Firm* — Edward J. Baba; Shweta Chandra; Bozicevic, Field & Francis LLP

(57) ABSTRACT

In vivo and ex vivo positionable magnetic filtration devices are provided that magnetically filter one or more therapeutic agents conjugated to a magnetic particle in blood flowing in a blood vessel.

25 Claims, 18 Drawing Sheets

(51) Int. Cl.
  *A61L 29/04* (2006.01)
  *A61K 47/69* (2017.01)
  *A61K 31/704* (2006.01)
  *A61K 41/00* (2020.01)
  *A61K 51/12* (2006.01)

(52) U.S. Cl.
  CPC ...... *A61K 47/6929* (2017.08); *A61K 51/1244* (2013.01); *A61L 29/04* (2013.01); *A61M 1/3615* (2014.02); *A61F 2/011* (2020.05); *A61F 2210/009* (2013.01); *A61F 2250/0014* (2013.01); *A61M 2202/0468* (2013.01); *A61M 2205/04* (2013.01)

(56) References Cited

U.S. PATENT DOCUMENTS

| | | | | |
|---|---|---|---|---|
| 5,980,479 | A * | 11/1999 | Kutushov | B03C 1/01 604/5.04 |
| 6,157,281 | A | 12/2000 | Katznelson et al. | |
| 10,064,653 | B2 * | 9/2018 | Vermesh | A61B 5/6851 |
| 2002/0133115 | A1 * | 9/2002 | Gordon | A61L 29/16 604/96.01 |
| 2003/0120202 | A1 * | 6/2003 | Gordon | A61M 1/3615 604/28 |
| 2008/0124779 | A1 | 5/2008 | Oh et al. | |
| 2013/0197296 | A1 * | 8/2013 | Ott | A61N 2/004 600/12 |
| 2013/0267762 | A1 * | 10/2013 | Levy | A61L 29/14 600/12 |
| 2014/0212335 | A1 * | 7/2014 | Lee | A61L 2/00 422/30 |

* cited by examiner

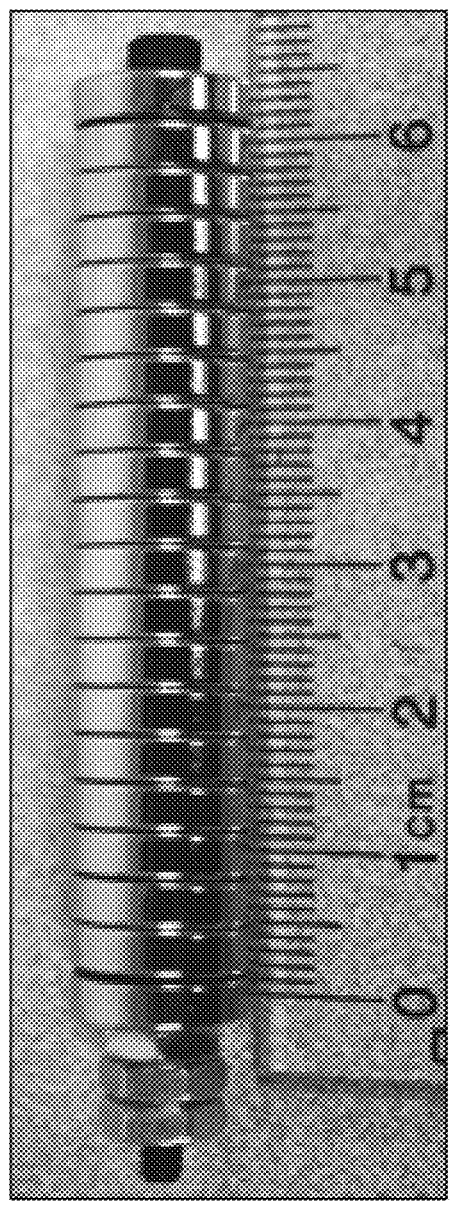
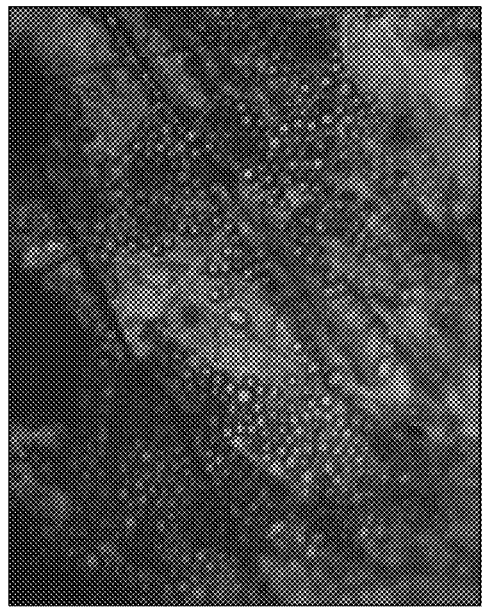
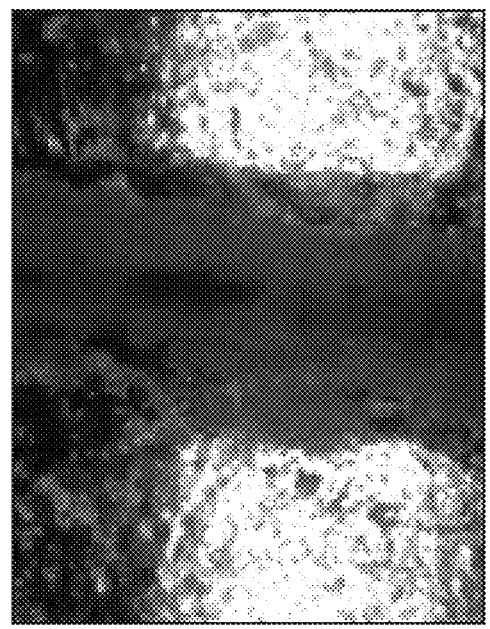
FIG. 2

MAGNETIC FILTRATION DEVICES AND METHODS RELATED THERETO

CROSS REFERENCE TO RELATED APPLICATIONS

This application claims the benefit of U.S. Provisional Application No. 62/117,322, filed Feb. 17, 2015, and U.S. Provisional Application No. 62/193,503, filed Jul. 16, 2015, which applications are incorporated herein by reference in their entirety.

STATEMENT REGARDING FEDERALLY SPONSORED RESEARCH

This invention was made with government support under grant no. R01 CA194533, awarded by the National Institutes of Health. The government has certain rights in the invention.

INTRODUCTION

Dosing of drugs ranging from cancer chemotherapeutics to anti-microbials to thrombolytics is currently limited by systemic side effects. As such, it is desirable to develop a new class of image-guided temporarily deployed endovascular medical devices that selectively remove specific drugs from the blood stream in order to reduce systemic toxicities. During the clinically standard interventional radiology (IR) approach of image guided intra-arterial chemotherapy (IAC) administration to a tumor containing organ, excess drug that is not immediately trapped in the target passes through the organ's draining veins, then into the systemic circulation, and then to the rest of the body where it causes systemic toxicities.

SUMMARY OF THE INVENTION

In some aspects of the present disclosure, in vivo positionable magnetic filtration devices are provided for filtering one or more therapeutic agents in blood flowing in a blood vessel. In some embodiments, the filtration device includes an elongated member, and a plurality of magnetic members coupled to the elongated member, where the elongated member and the plurality of magnetic members are dimensioned for positioning within a blood vessel of a human or non-human animal, and where the plurality of magnetic members comprises a magnetically attractable material to bind a magnetic particle sound to a therapeutic agent from blood.

In some aspects of the present disclosure, systems for treating a subject are provided, where the system includes a therapeutic agent conjugated to a magnetic particle and an in vivo positionable magnetic filtration device for filtering one or more therapeutic agents in blood flowing in a blood vessel are provided. In some embodiments, the filtration device includes an elongated member, and a plurality of magnetic members coupled to the elongated member, where the elongated member and the plurality of magnetic members are dimensioned for positioning within a blood vessel of a human or non-human animal, and where the plurality of magnetic members comprises a magnetically attractable material to bind a magnetic particle sound to a therapeutic agent from blood.

In some aspects of the present disclosure, methods of in vivo magnetic filtration of a magnetic particle conjugated therapeutic agent are provided. In some embodiments, the method includes positioning a magnetic filtration device in a blood vessel of a body of a human or non-human animal, the filtration device positioned downstream from a target tissue site, the filtration device for magnetically filtering the magnetic particle conjugated therapeutic agent in the blood flowing in the blood vessel, and administering a therapeutic agent conjugated to a magnetic particle upstream from the target tissue site to direct flow of the therapeutic agent to the target tissue site and then to the magnetic filtration device, where the in vivo positioned magnetic filtration device magnetically binds the magnetic particles conjugated to the therapeutic agent as the blood and the therapeutic agent are received by the magnetic filtration device.

In still further aspects of the present disclosure, methods of ex vivo magnetic filtration of a magnetic particle conjugated therapeutic agent are provided. In some embodiments, the method includes connecting an ex vivo magnetic filtration device in fluid communication with a blood vessel of a body of a human or non-human animal at a connection point downstream from a target tissue site for magnetically filtering the magnetic particle conjugated therapeutic agent in the blood flowing in the blood vessel, administering a therapeutic agent conjugated to a magnetic particle upstream from the target tissue site to direct flow of the therapeutic agent to the target tissue site and then to the magnetic filtration device, assisting the blood to flow ex vivo and contact the ex vivo magnetic filtration device, such that the magnetic filtration device magnetically binds the magnetic particles conjugated to the therapeutic agent as the blood and the therapeutic agent are received by the magnetic filtration device, and assisting the filtered blood to flow back into the blood vessel of the body of the human or non-human animal.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2 shows an Initial larger magnetic filtration device before (Panel A) and after (Panels B and C) preliminary flow chamber infusion experiments with adherent 5 micron ferrous particles. 5× (Panel B) and 50× (Panel C) light microscopy images of nanoparticles adherent to the magnetic filtration device prototype after preliminary flow chamber infusion experiments. The magnetic filter is able to extract ferromagnetic particles from solution in vitro.

FIG. 11, Panel B shows the results of the continuous flow setup according to certain embodiments.

FIG. 12, Panel B shows a TLC graph with radioactivity along the magnetic filtration device according to certain embodiments. FIG. 12, Panel C shows the results of the single flow setup according to certain embodiments.

DETAILED DESCRIPTION OF THE INVENTION

Figure 1:
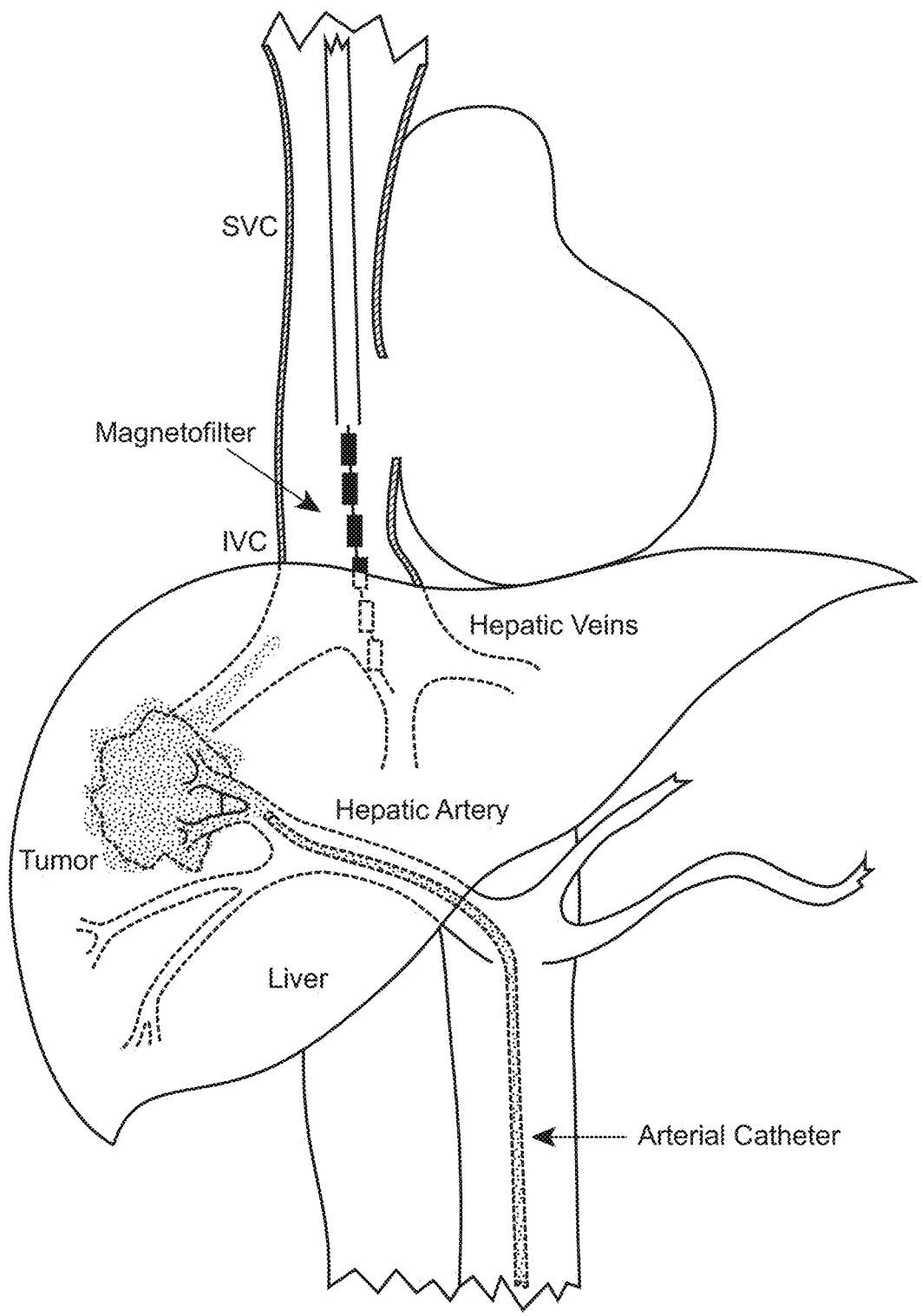
FIG. 1 shows a Hepatic IAC procedure with a magnetic filtration device. From a percutaneous femoral arterial approach, a microcatheter is guided into the arteries feeding the liver tumor to directly inject MTC-Dox or SPIO-Dox (IAC procedure). From a percutaneous jugular venous approach, the MagnetoFilter device is guided through the superior vena cava (SVC) and deployed in the veins draining the liver proximal to the heart (the site of dose-limiting systemic toxicity).

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a device" includes a plurality of such devices and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Magnetic Filtration Devices

Dosing of drugs is generally limited by systemic toxic side effects. Intraarterial chemotherapy (IAC) permits delivery of therapeutics at high concentration to a target organ, but systemic toxicities often still limit dosing when the therapeutic agent exits the target organ via venous drainage. Currently, the predominant ways drugs are eliminated from the bloodstream are via natural metabolic pathways or through invasive measures like hemodialysis that pump blood out of the body for filtration in a large extracorporeal device. Described herein is a new class of image-guided temporarily deployed in vivo, e.g., endovascular, medical devices that selectively remove specific drugs or therapeutic agents from the blood stream in situ in order to reduce systemic toxicities and thereby increase the safety and efficacy of locoregional drug therapy.

Magnetic filtration devices of interest sequester magnetic particles, such as iron oxide particles, bound to chemotherapeutic agents (e.g., magnetically targeted carrier linked doxorubicin (MTC-Dox) or superparamagnetic iron oxide linked doxorubicin (SPIO-Dox)) to remove excess particles from the draining venous system during intra-arterial chemotherapy administration. Analogous to a central venous catheter or inferior vena cava filter, the magnetic filter would be placed into the draining venous system using, for example, x-ray fluoroscopic image guidance prior to an IAC infusion, would remain in place during IAC infusion, and would be removed from the body along with all of the captured particles/agents through its access sheath shortly following IAC.

In embodiments, the magnetic filtration device includes one or more magnets configured to attract particles susceptible to a magnetic force (e.g., magnetic attraction). In some embodiments, the subject magnetic filtration devices include one or more magnetic field sources configured to produce a magnetic field. In certain instances, the magnetic field source produces a magnetic field having a magnetic field gradient, such that the strength of the magnetic field differs relative to the position within the magnetic field. For example, the generated magnetic field may possess a magnetic field that is greater in a first location and decrease in locations further from the first location.

Depending on the magnetic particle bound therapeutic agent (described in greater detail below), the magnetic field source in the subject magnetic filtration device varies in magnetic field strength and magnetic field gradient. In certain embodiments, the force the magnetic field is able to exert on the magnetic particle is proportional to the magnetic field strength and the magnetic field gradient. In some cases, the magnetic field source is configured to produce a magnetic field having a magnetic force sufficient to separate magnetic particle bound therapeutic agents form non-magnetic particle bound and non-magnetic components. For example, the magnetic field source may be configured to produce a magnetic field having a magnetic field gradient such that the product of the magnetic field and the magnetic field gradient is sufficient to separate magnetic particle bound therapeutic agents from non-magnetic particle bound and non-magnetic components in the blood stream (e.g., intra-arterial, as described in greater detail below).

The magnetic filtration device may include a magnetic field source having any suitable shape that facilitates separation of magnet particle bound therapeutic agent from non-magnetic particle bound components as well as non-magnetic compounds. In certain embodiments, the magnetic field source of the magnetic filtration device is an elongated magnetic field source having a longitudinal length that is greater than its transverse width. The longitudinal length of each magnet may vary depending on the type of magnet used and magnetic field strength desired and may be 1 mm or more, such as 2 mm or more, such as 3 mm or more, such as 4 mm or more, such as 5 mm or more, such as 7.5 mm or more, such as 10 mm or more, such as 15 mm or more, such as 20 mm or more, such as 25 mm or more, such as 50 mm or more, such as 75 mm or more and including 100 mm or more. In certain embodiments, each magnetic member has a length of 5 mm to 10 mm.

The cross sectional shape of the magnets may vary as desired and may include but is not limited to rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The cross-sectional dimensions of the magnets varies, ranging from 0.01 µm to 50 mm, such as from 0.05 µm to 40 mm, such as from 0.1 µm to 30 mm, such as from 0.5 µm to 20 mm, such as from 1 µm to 10 mm, such as from 2.5 µm to 7.5 mm, such as from 5 µm to 7 mm, such as from 10 µm to 6.5 mm, such as from 25 µm to 6 mm, such as from 50 µm to 5.5 mm, such as from 100 µm to 5 mm, such as from 500 µm to 4.5 mm, such as from 750 µm to 4 mm and including from 1 mm to 2.5 mm. In certain embodiments, each magnet is cylindrical and has a circular cross-sectional shape. In these embodiments, each magnet has a diameter which varies, ranging from 0.01 µm to 50 mm, such as from 0.05 µm to 40 mm, such as from 0.1 µm to 30 mm, such as from 0.5 µm to 20 mm, such as from 1 µm to 10 mm, such as from 2.5 µm to 7.5 mm, such as from 5 µm to 7 mm, such as from 10 µm to 6.5 mm, such as from 25 µm to 6 mm, such as from 50 µm to 5.5 mm, such as from 100 µm to 5 mm, such as from 500 µm to 4.5 mm, such as from 750 µm to 4 mm and including a diameter of from 1 mm to 2.5 mm.

In some embodiments, the magnetic filtration device includes a magnetic field source that is shaped so that the flow of magnetic particle bound therapeutic agent is proximal to the magnetic field source which minimizes the distance between the magnetic field source and the flowing particles. This will increase, where desired, the retention of magnetic particle bound therapeutic agents. In other embodiments, the magnetic filtration device includes a magnetic field source that is shaped to maximize the contact between the flowing magnetic particle bound therapeutic agents with the magnetic filtration device. In these embodiments, the magnetic field source is shaped such that the flow of magnetic particle bound therapeutic agent is substantially parallel to the longitudinal axis of the magnetic field source.

In embodiments, the magnetic filtration device may any suitable number of magnetic field sources, as desired, such as a single magnetic field source, such as 2 or more magnetic field source, such as 3 or more, such as 4 or more, such as 5 or more, such as 10 or more, such as 15 or more, such as 25 or more, such as 35 or more and including 50 or more magnetic field sources. In embodiments, the magnetic field source may be a permanent magnetic, an electromagnet, a superconducting magnet or a combination thereof. In certain embodiments, magnetic filtration devices include one or more permanent magnets. The term "permanent magnet" is used herein in its conventional sense to refer to a magnetic material that has a persistent magnetic field such that the magnetic field does not substantially decrease over time. In other embodiments, the magnetic filtration device includes one or more "soft" magnet, employing a material that can be magnetized in the presence of an applied external magnetic field, but where the magnetic field strength decreases over time as compared to a permanent magnet.

In some embodiments, magnetic filtration devices of interest include two or more magnets aligned in series along a longitudinal axis and configured for insertion into the vasculature of a subject (e.g., artery, vein, etc.). Each magnet may be spaced apart from one another by 0.001 mm or more, such as by 0.005 mm or more, such as by 0.01 mm or more, such as by 0.05 mm or more, such as by 0.1 mm or more, such as by 0.5 mm or more, such as by 1 mm or more, such as 2 mm or more, such as by 3 mm or more, such as by 4 mm or more, such as by 5 mm or more, such as by 6 mm or more, such as by 7 mm or more, such as by 8 mm or more, such as by 9 mm or more, such as by 10 mm or more, such as by 12.5 mm or more, such as by 15 mm or more, such as by 25 mm or more and including by 50 mm or more. Depending on the number of magnets, the spacing between each magnet may be the same, different, or a combination thereof as desired. In certain embodiments, the spacing between each magnet is the same. In other embodiments, the spacing between each magnet is different. In yet other embodiments, the spacing between some magnets is the same and the spacing between some magnets is different.

In certain instances, magnetic filtration devices of interest include a spacer between each magnet. In these embodiments, instead of empty space between each magnet, separation between each magnetic in the subject magnetic filtration device includes a spacer component. Any suitable material may be used as a spacer, including but not limited to rubber, plastic, glass or other non-magnet material. In certain embodiments, the plurality of magnets in the subject magnetic filtration device are separated by rubber spacers. Depending on the space between each magnet desired, the size of each spacer may vary, such as where each spacer is individually 0.001 mm or more, such as by 0.005 mm or more, such as by 0.01 mm or more, such as by 0.05 mm or more, such as by 0.1 mm or more, such as by 0.5 mm or more, such as by 1 mm or more, such as 2 mm or more, such as by 3 mm or more, such as by 4 mm or more, such as by 5 mm or more, such as by 6 mm or more, such as by 7 mm or more, such as by 8 mm or more, such as by 9 mm or more, such as by 10 mm or more, such as by 12.5 mm or more, such as by 15 mm or more, such as by 25 mm or more and including by 50 mm or more. The size of each spacer may be the same, different, or a combination thereof as desired. In certain embodiments, the size of the spacers between each magnet is the same. In other embodiments, the size of the spacer between each magnet is different. In yet other embodiments, the size of the spacer between some magnets is the same and the size of the spacer between some magnets is different.

In some embodiments, magnetic filtration devices of interest may include two or more series of longitudinally aligned magnets, such as two or more series of longitudinally aligned magnets having parallel longitudinal axes, such as three or more, such as four or more and including five or more series of longitudinally aligned magnets having parallel longitudinal axes.

Figure 6:
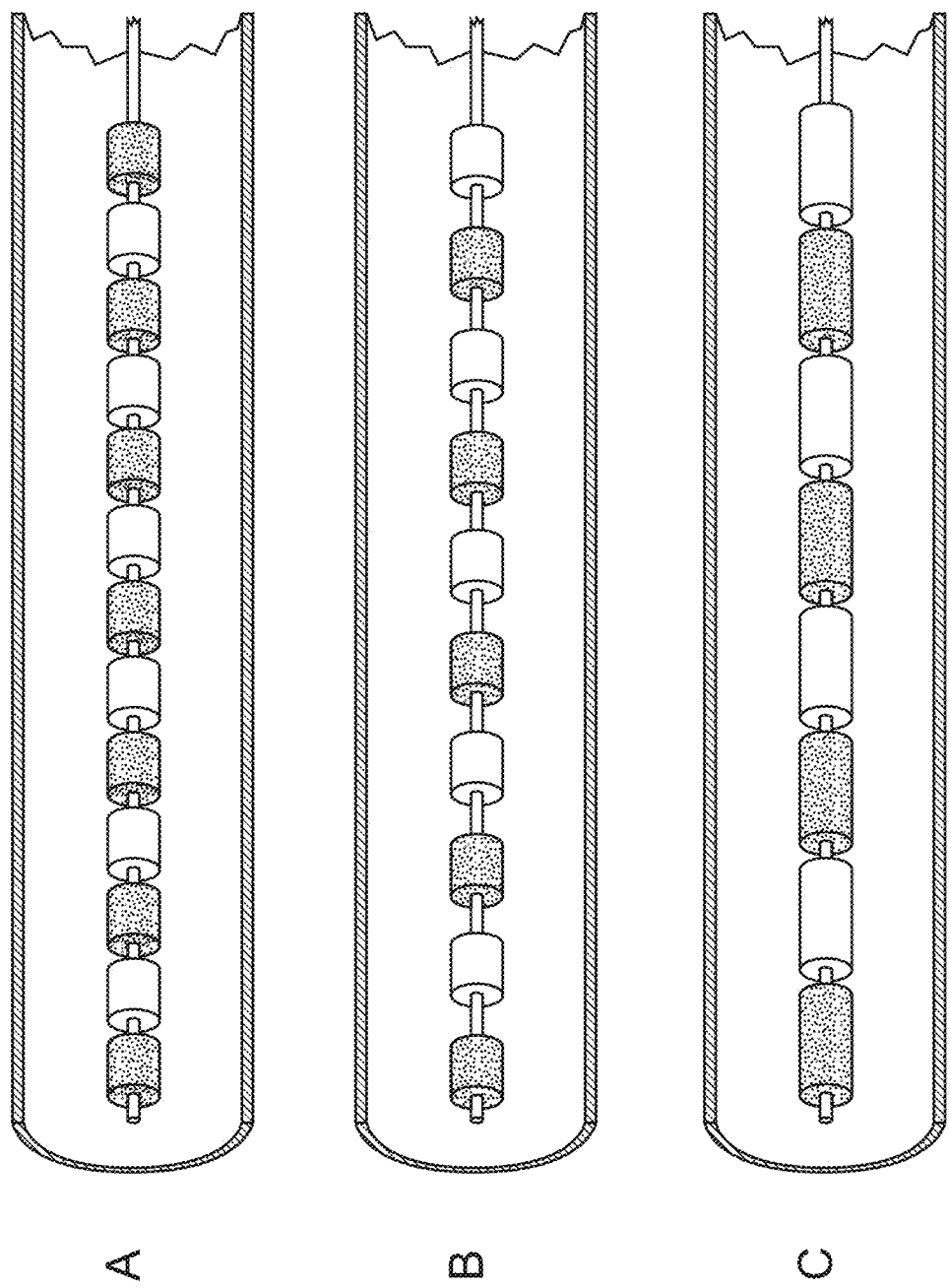
FIG. 6, Panels A-C depict a plurality of magnets in a magnetic filtration device according to certain embodiments.
Figure 7:
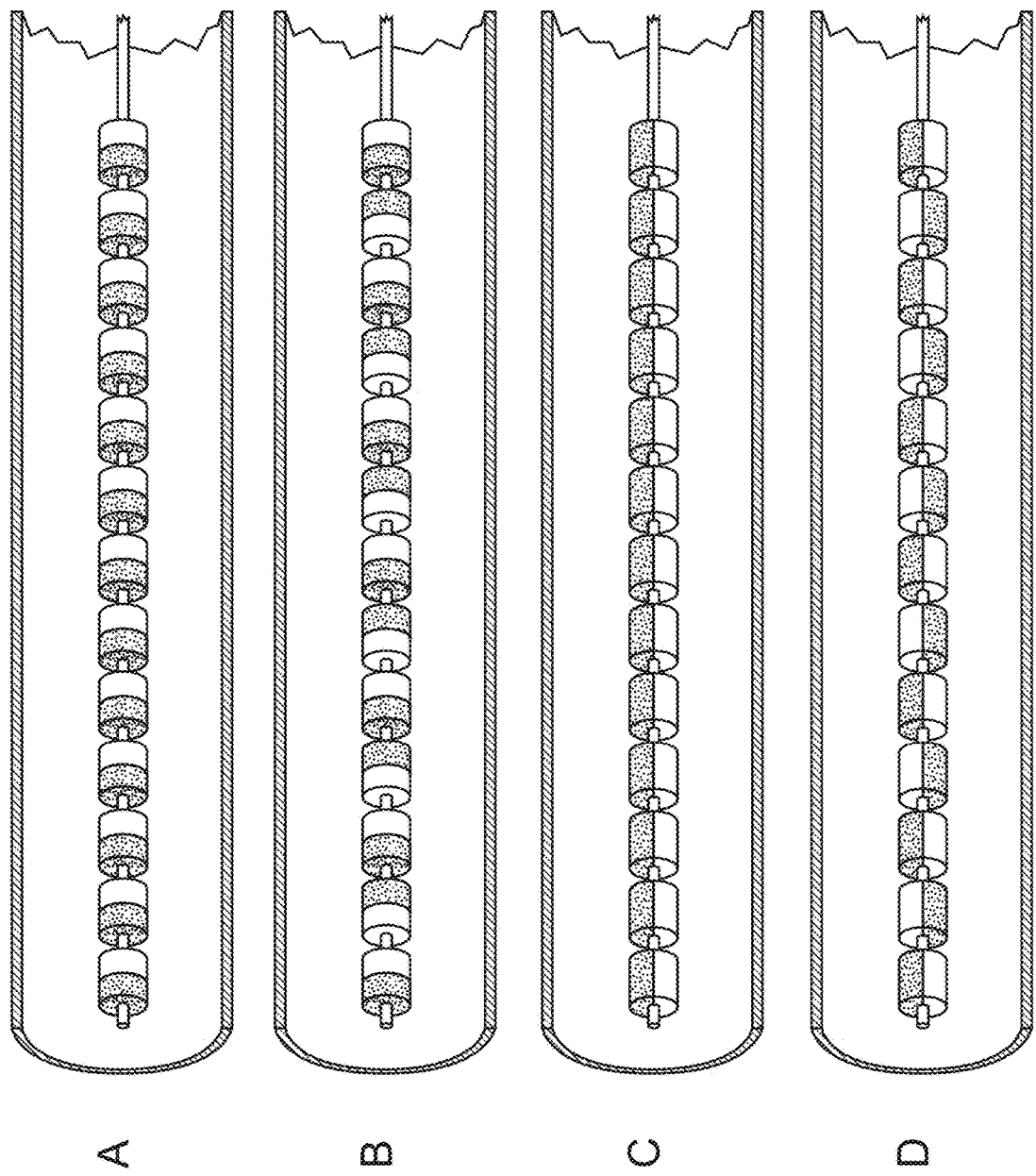
FIG. 7, Panels A-D depict arrangements of magnets in the magnetic filtration device according to certain embodiments.

FIGS. 6A-6C depict a plurality of magnets in a magnetic filtration device according to certain embodiments. FIG. 6A depicts a series of magnets each having the same size and spaced apart from each other uniformly. FIG. 6B depicts a series of magnets each having the same size and spaced apart from each other uniformly but with a greater space between each magnet as compared to the spacing shown in FIG. 6A. FIG. 6C depicts magnets having a longer longitudinal dimension than the magnets shown in FIGS. 6A and 6B and uniformly spaced apart. The spacing between the magnets in FIG. 6C is equivalent to the spacing shown in FIG. 6A but shorter than the spacing between magnets shown in FIG. 6B.

Where the magnetic filtration device includes two or more permanent magnets, the magnets may be arranged in various different configurations, as desired. In certain embodiments, the magnets are arranged where magnetization is across the length aligned (LA). In other embodiments, the magnets are arranged where magnetization is across length opposed with like polarities together (LO). In yet other embodiments, the magnets are arranged where magnetization is across the diameter aligned (DA). In still other embodiments, the magnets are arranged where magnetization is across the diameter opposed (DO). FIGS. 7A-7D depict arrangements of magnets in the magnetic filtration device according to certain embodiments. FIG. 7A depicts magnets of the magnetic filtration device configured where magnetization is across length and aligned. FIG. 7B depicts magnets of the magnetic filtration device configured where magnetization is across length and opposed with like polarities arranged together. FIG. 7C depicts magnets of the magnetic filtration device configured where magnetization is across diameter and aligned. FIG. 7D depicts magnets of the magnetic filtration device configured where magnetization is across diameter and opposed.

Figure 8:
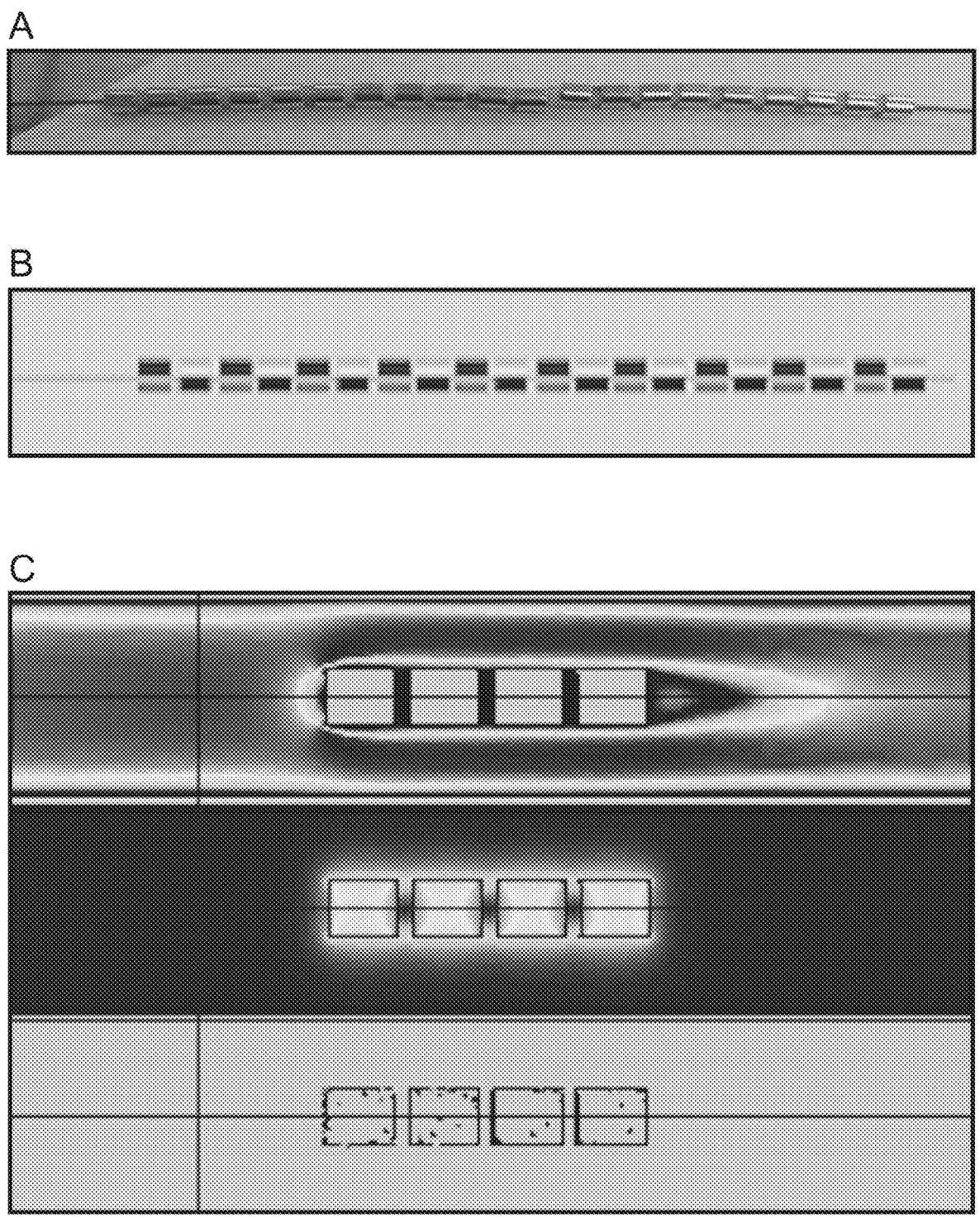
FIG. 8, Panels A-C depict a magnetic filtration device having magnets that are arranged where magnetization is across diameter in an alternating orientation according to certain embodiments. Additionally there is assessment of laminar flow around the device, magnetic field generated, and particle capture by the device.

FIGS. 8A-8C depict a magnetic filtration device having magnets that are arranged where magnetization is across diameter in an alternating orientation according to certain embodiments. FIG. 8A depicts a photograph of the magnetic filtration device. FIG. 8B depicts a CAD image of the magnetic filtration device. FIG. 8C depicts COMSOL simulations of laminar flow around the device, magnetic field generated by the device and particles captured on the device.

Figure 9:
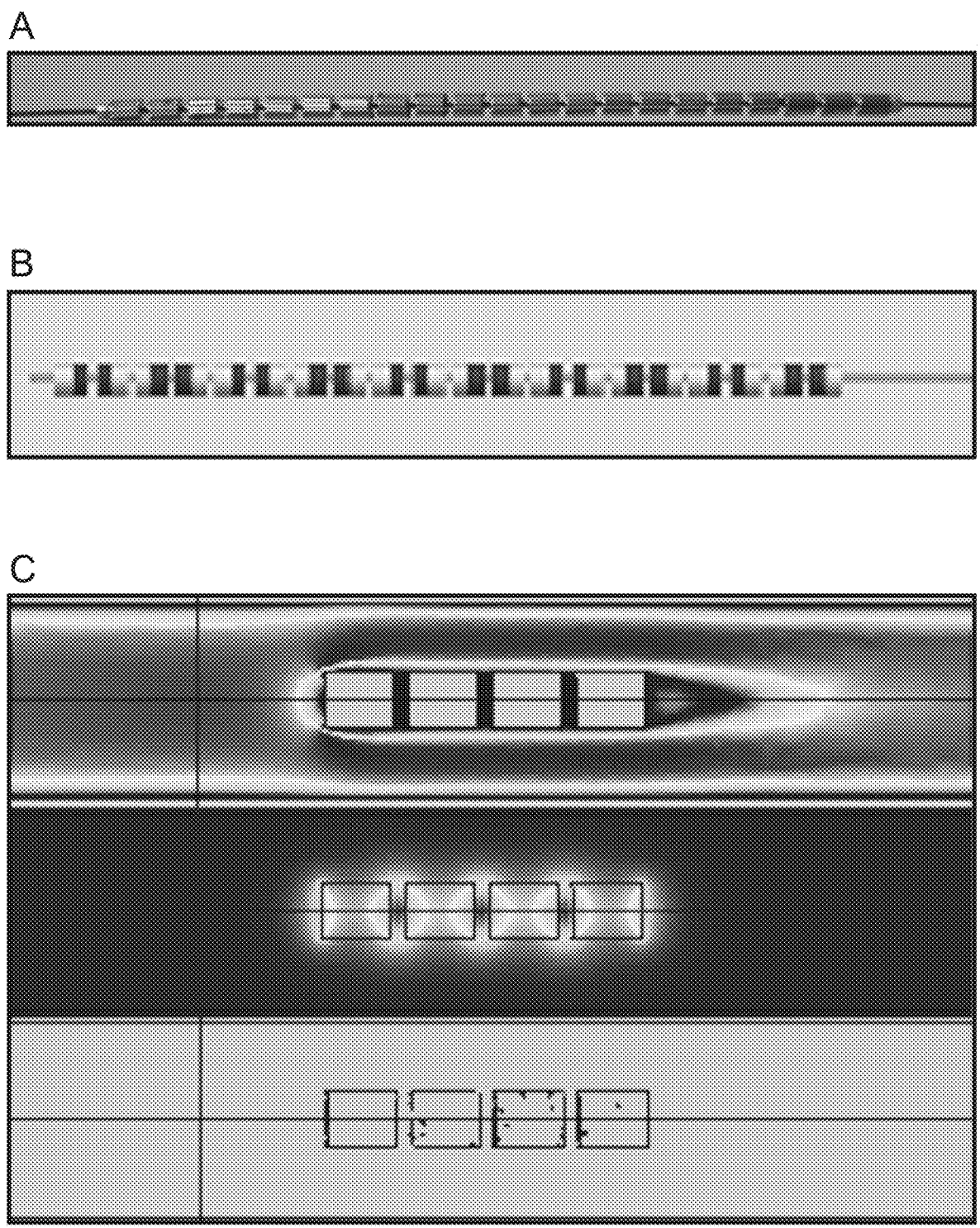
FIG. 9, Panels A-C depict a magnetic filtration device having magnets that are arranged where magnetization is across length in an alternating orientation according to certain embodiments. Additionally there is assessment of laminar flow around the device, magnetic field generated, and particle capture by the device.

FIGS. 9A-9C depict a magnetic filtration device having magnets that are arranged where magnetization is across length in an alternating orientation according to certain embodiments. FIG. 9A depicts a photograph of the magnetic filtration device. FIG. 9B depicts a CAD image of the magnetic filtration device. FIG. 9C depicts COMSOL simulations of laminar flow around the device, magnetic field generated by the device and particles captured on the device.

Figure 10:
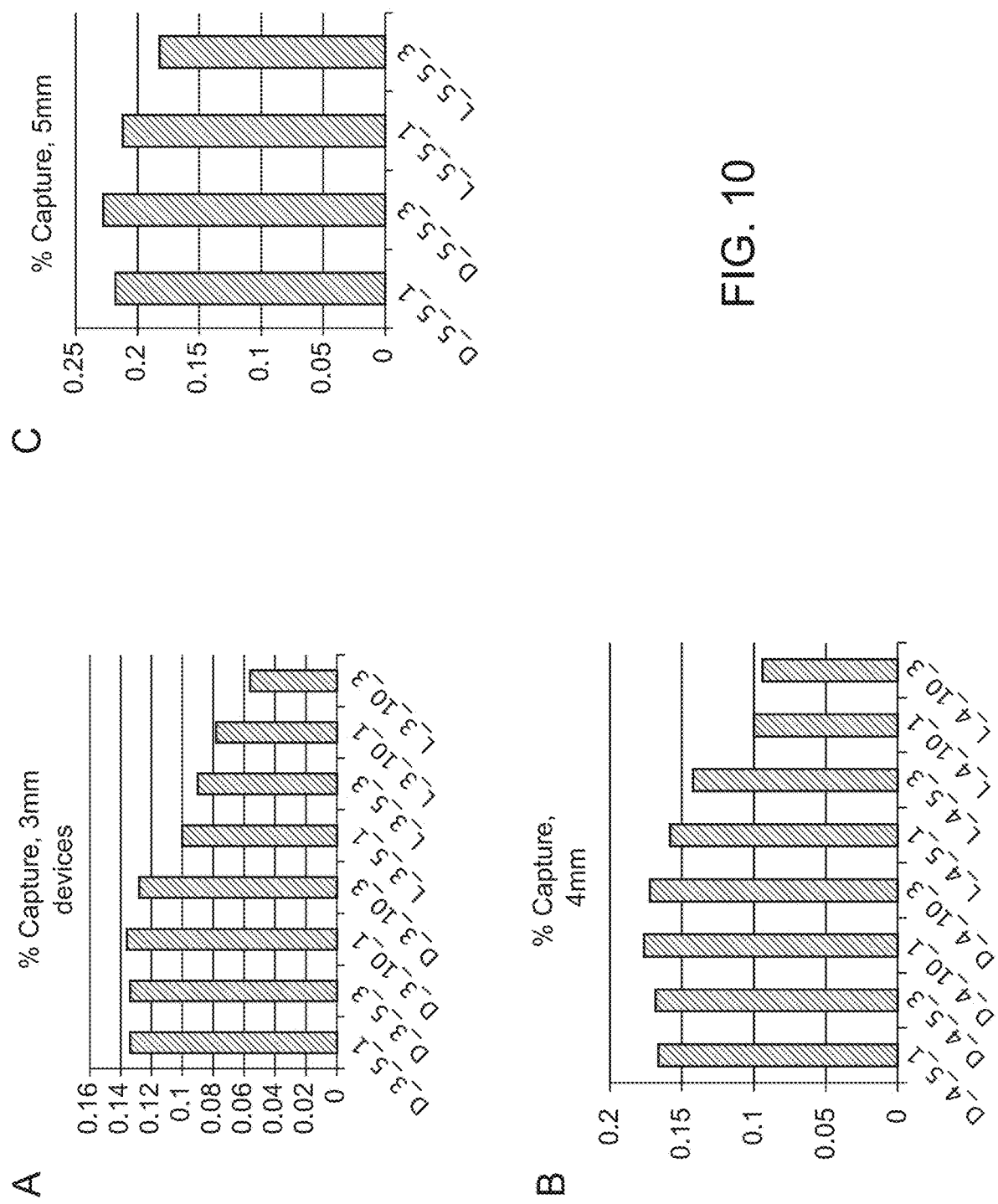
FIG. 10, Panels A-C depict the percent capture of particles by the magnetic filtration device in particle tracing simulation according to certain embodiments.

FIGS. 10A-10C depict the percent capture of particles by the magnetic filtration device in particle tracing simulation according to certain embodiments. FIGS. 10A-10C illustrate percent capture of 1500 particles by a 3 mm magnetic filtration device, a 4 mm magnetic filtration device and a 5 mm magnetic filtration device. The x-axis of FIGS. 10A-10C are coded by magnetization orientation (L or D), diameter of magnets (mm), length of magnets (mm) and spacing between magnets (mm).

Depending on the magnetic particles bound to the therapeutic agents and type of vasculature of the subject, the magnetic field source may produce a magnetic field having a magnetic field flux density that varies, such as 0.0001 T or more, such as 0.0005 T or more, such as 0.001 T or more, such as 0.005 T or more, such as 0.01 T or more, such as 0.05 T or more, such as 0.1 T or more, such as 0.5 T or more, such as 1 T or more and including 1.5 T or more. For example, the magnetic field flux density may range from 0.0001 T to 2 T, such as from 0.001 T to 1.9 T, such as from 0.01 T to 1.8 T, such as from 0.1 T to 1.7 T, such as from 0.5 T to 1.6 T and including from 1 T to 1.5 T.

During locoregional intraarterial (IA) infusion of therapeutic agents (e.g., the chemotherapeutic doxorubicin) linked to a magnetically responsive particle, such as iron oxide particles (e.g., superparamagnetic iron oxide nanoparticles, SPIOs, or larger magnetically targeted carriers, MTCs), a significant fraction of the conjugated therapeutic particles (MTC-Dox, SPIO-Dox) pass through a targeted tumor into the veins draining the organ in which the tumor is located. Just prior to IA infusion of magnetic therapeutic particles, a magnetic filtration device is position in vivo, via, for example real time x-ray angiography guidance into the vein or veins draining the target organ. The magnetic filtration then captures, via magnetic attraction, magnetic particles passing through the target organ during and immediately following IA infusion. Finally, the magnetic filtration device is removed from the patient within a few minutes after the IA infusion procedure, thus eliminating the magnetic particles from the patient. This approach reduces systemic toxicity and thereby permit dose escalation during locoregional IA therapy. The fundamental challenge to IAC is to remove a specific agent from the blood in veins draining an organ undergoing image guided IA chemotherapy infusion, after the agent has had a chance to have a therapeutic effect in the target organ and before it can cause systemic toxic effects. The magnetic attraction strategy has demonstrated very promising results and offers excellent specificity for removing therapeutic magnetic particles from the blood without removing nontarget endogenous blood components, which are essentially nonmagnetic.

Although the overall approach of paired intraaterial infusion and venous filtration can theoretically be used for any drug or therapeutic agent, the most compelling initial application for this technology is increasing efficacy and safety of locoregional cancer chemotherapy. In certain embodiments, the magnetic filtration device is used in the treatment of patients with hepatocellular carcinoma (HCC). Image-guided transarterial chemoembolization (TACE), a form of IAC, is performed in IR and is a standard of care for unresectable primary and secondary hepatic malignancies. TACE increases survival compared to best supportive treatments in this population in a cost-effective manner. IAC is performed by navigating microcatheters into the arteries supplying tumors and directly delivering chemotherapy. In addition to treatment of HCC, IAC has been a successful palliative measure for thousands of patients with liver metastases and is of interest in cancers elsewhere in the body including infusion of nanoparticles to treat head and neck cancer. Doxorubicin (Dox) use is limited by systemic toxicities, consisting of bone marrow suppression, hair loss, gastrointestinal toxicity, and irreversible cardiac failure. Toxicity remains problematic in IAC since first pass hepatic clearance of Dox ranges from only 50-70% regardless of infused dose. Dox follows a therapeutic linear dose-response model, in which increasing dose linearly increases tumor cell kill, providing motivation for higher-dose Dox therapy.

Magnetic Particle Bound Therapeutic Agent

The therapeutic agent that is conjugated to a magnetic material/particle may include, for example, any variety of agents, such as drugs or chemical substances used in the treatment, cure, prevention, or diagnosis of disease or used to otherwise enhance physical or mental well-being. The therapeutic agent may include, for example, chemotherapeutic agents and/or non-chemotherapeutic agents. In one embodiment, the therapeutic agent is Dox and used to treat cancerous tissue, such as within an organ. Non-chemotherapeutic agents may include, but are not limited to, for example, anti-coagulants, thrombolytics, etc. The thrombolytic may be used, for example, in stroke treatment.

The expression "magnetic material" is used herein to refer to a material that when exposed to a magnetic field either heats or physically moves. Preferably the magnetic material takes the form of a magnetic particle, for example a micro- or nano-particle. As such, magnetic particles generally refer to particles that display magnetic properties.

The magnetic material may be inherently magnetic or, alternatively, may be one which reacts in a magnetic field. The magnetic material may be ferromagnetic, antiferromagnetic, ferrimagnetic, antiferrimagnetic or superparamagnetic. The magnetic material may include elemental iron, chromium manganese, cobalt, nickel, or a compound thereof. The iron compound may be an iron salt which may be selected from the group which includes magnetite ($Fe_3O_4$), maghemite (gamma-$Fe_2O_3$) and greigite ($Fe_3S_4$), or any combination thereof.

The magnetic particles of the present disclosure can also have various sizes. In some embodiments, the magnetic particles of the present disclosure may include magnetic nanoparticles. In some embodiments, the magnetic nanoparticles can have sizes that range from about 0.1 nm to about 1000 nm. In some embodiments, the magnetic nanoparticles can have sizes that range from about 0.5 nm to about 200 nm. In some embodiments, the magnetic nanoparticles can have sizes that range from about 50 nm to about 100 nm. In some embodiments, magnetic nanoparticles can have sizes that range from about 10 nm to about 30 nm.

Various methods may also be used to make magnetic particles. For instance, a wide range of syntheses of magnetite (iron oxide) are known. See, e.g., C. A. Crouse and A. R. Barron, J. Mater. Chem., 2008, 18, 4146. Many of these synthetic approaches can be used for mixed metal oxide particles described above. Such syntheses can result in metal oxide particles that are surface stabilized or functionalized with a molecular group, often based upon a carboxylic acid, that allow for their miscibility or solubility in a desired medium. In some embodiments, starting materials (e.g., iron acetylacetonate and cobalt acetylacetonate) are combined with a specific starting ratio (e.g., ratios given in millimoles (mmol)). To this is added, also in predetermined ratios, oleic acid, oleylamine, 1,2-hexadecanediol and benzyl ether. The oleic acid and oleylamine act as surfactants. The 1,2-hexadecanediol is used to either promote nucleation or limit growth, allowing for small particles that are monodisperse to be formed. In some embodiments, benzyl ether can be used as the solvent. After the reaction is run and the particles are cleaned and suspended in hexanes, analysis can be performed in order to obtain the ratio of iron to the other metal in the particles. Such modes of nanoparticle synthesis are described in more detail in the Examples herein. Though such methods are known, there has been no previous attempt to determine a correlation between starting ratios and end product ratios in order to control the properties of magnetic particles. In some embodiments, magnetic nanoparticles may be radioactively labeled for tracking and visualization with elements including, but not limited to, Zr-89 and Cu-64.

A chemotherapeutic agent may be an agent selected from the group consisting of S phase dependent antimetabolics, capercitabine, cytarabine, doxorubicin, fludarabine, floxuridine, fluorouracil, gemcitabine, hydroxyurea, mercaptopurine, methotrexate, prednisone, procarbazine, thioguanine, M phase dependent vinca alkaloids, vinblastine, vincristine, vinorelbine, podophyllotoxins, etoposide, teniposide, taxanes, doxetaxel, paxlitaxel, G2 phase dependent, bleomycin, irinotecan, mitoxantrone, topotecan, G1 phase dependent, asparaginase, corticosteroids, alkylating agents, nitrogen mustards, mechlorethamine, mustargen, cyclophosphamide, ifosfamide and clorambucil, leukeran, nitrosoureas, platinum agents, cisplatin, platinol, carboplatin, paraplatin, antimetabolites, natural therapeutic products, antitumour antibiotics, anthracyclines, epipodophyllotoxins, vinca alkaloids, taxanes, camptothecin, melphalan, carmusline, methotrexate, 5-fluorouracil, mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate or a combination thereof.

The chemotherapeutic or radiotherapeutic agent may be associated with an antibody, for example a monoclonal antibody.

The therapeutic agent may include DNA, RNA, interfering RNA (RNAi), a peptide, polypeptide, an antibody for example a monoclonal antibody or an antibody fragment such as a single chain antibody fragment, an aptamer, a small molecule. Small molecules may include, but are not limited to, peptides, peptidomimetics (e.g. peptoids), amino acids, amino acid analogs, polynucleotides, polynucleotide analogs, nucleotides, nucleotide analogs, organic or inorganic compounds (i.e. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Methods

In some aspects of the present disclosure, methods of in vivo and ex vivo magnetic filtration of one or more therapeutic agents are provided. The methods include positioning a magnetic filtration device in a blood vessel of a body of a human or non-human animal, and administering a therapeutic agent upstream from the target tissue site to direct flow of the therapeutic agent to the target tissue site and then to the magnetic filtration device. The magnetic filtration device is positioned downstream from a target tissue site. For example, the magnetic filtration device may be positioned 5 mm or more downstream from the target tissue site, such as 10 mm or more, such as 15 mm or more, such as 25 mm or more, such as 30 mm or more, such as 50 mm or more, such as 75 mm or more, such as 100 mm or more, such as 150 mm or more, such as 200 mm or more, such as 250 mm or more, such as 300 mm or more, such as 400 mm or more, such as 500 mm or more and including 600 mm or more downstream from the target site. In certain embodiments, the magnetic filtration device is placed at a position ranging from 10 mm to 500 mm downstream from the target site, such as from 25 mm to 400 mm, such as from 30 mm to 300 mm, such as positioning the magnetic filtration device from 50 mm to 250 mm downstream from the target site. Further, the magnetic filtration device is for filtering the magnetic particle bound therapeutic agent in the blood flowing in the blood vessel. The in vivo positioned magnetic filtration device filters the therapeutic agent as the blood and the therapeutic agent are received by the filtration device. Various examples of positioned devices in different blood vessels include the hepatic vein, iliac vein, inferior vena cava, renal vein, and superior vena cava. Additional exemplary positioning of the present device also include, but are not limited to, intracranially in the dural venous sinuses (e.g., sigmoid sinus, transverse sinus, torcula, straight sinus, superior sagittal sinus) to remove agents during cerebral embolization or chemoinfusion; internal jugular vein with the device inserted, for example, either transfemorally or directly in the ipsilateral internal jugular vein, for head and neck tumors and during cerebral embolization or chemoinfusions; and the brachiocephalic vein between the superior vena cava and the internal jugular vein.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head (including brain) and neck, colon, skin and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

It should be appreciated that the methods may include the magnetic filtration devices described in the present disclosure, and for the sake of clarity and brevity, will not be described in great detail again, but rather reference is made to the previous discussion of these features. Additionally, the description of the methods of using the magnetic filtration devices is also applicable to the methods section, and will not be described again great detail again but rather reference is made to the previous discussion.

The target tissue may include, for example, cancerous or otherwise diseased tissue. The target tissue site should be accessible by the bloodstream and may include organs for instance. Example cancerous tissue sites may include, but are not limited to, the liver, kidney, brain, head/neck, skin gastrointestinal tract, and musculoskeletal system. For example, the target tissue site may include an organ afflicted with cancerous growths.

The therapeutic agent is administered upstream from the target tissue site—e.g., intraarterially or intravenously supplying a cancerous or otherwise diseased organ. In certain embodiments, the magnetic filtration device is positioned within a vein draining a target organ—e.g., an organ containing diseased or cancerous tissue—or a central vein. In some instances, for example, the magnetic filtration device may be inserted within an internal jugular or femoral vein. In some instances, the magnetic filtration device may be malleable to conform to the vein, such as the renal vein, hepatic vein, or vena cavae.

The distance the magnetic filtration device is positioned from the target tissue site may vary based on the particular blood vessel, the location of the target tissue site (e.g., which organ), etc. The distance to the target tissue site or organ including the target tissue may vary. For instance, example distances may include, but are not limited to, distances from two feet or less, such as 6 inches or less, including three inches or less. In one embodiment, the distance may be less than one inch from the target tissue site or organ including the target tissue. In other embodiments, the distance to the target tissue site or organ may be greater than two feet, such as up to four feet—e.g., if for instance, a tumor was present in person's extremity such as a toe and the magnetic filtration device placed in the inferior vena cava. It should be appreciated that the ranges are exemplary, and distances outside the example ranges provided are also possible.

In certain embodiments, the magnetic filtration device may be positioned in the blood vessel by inserting a catheter within the blood vessel downstream from the target tissue. In one embodiment, the magnetic filtration device is positioned within the catheter at the time the catheter is inserted within the blood vessel. In another embodiment, the catheter is first inserted within the blood vessel, and thereafter the magnetic filtration device is inserted within the lumen of the catheter. When inside the catheter, an elongated control member may be used by the operator to displace the filtration device within the lumen of the catheter until a portion of the filtration device is displaced out the distal end of the catheter and into the blood vessel. The magnetic filtration device may include a frame structure that expands to occupy the entire cross sectional area of the blood vessel when the frame structure is displaced out the distal end of the catheter. The elongated control member may also be used by the operator to retract and constrain the exposed portion of the magnetic filtration device back inside the catheter.

In certain embodiments, the magnetic filtration device is removable from the catheter during use—e.g., while the catheter is still positioned inside the blood vessel. In some instances, the magnetic filtration device may be sterilized and reusable. In other instances, the magnetic filtration device may be disposable and a replacement magnetic filtration device may be inserted into the catheter after the original magnetic filtration device is discarded. The replacement magnetic filtration device is then displaced within the catheter until a portion of the replacement magnetic filtration device is displaced out the distal end of the catheter, and the magnetic filtration process repeated with the replacement magnetic filtration device.

It should be appreciated that the frame structure may be part of the catheter or independently positioned within the catheter. Furthermore, the elongated control member and magnetic elements, may be part of the frame structure or removably coupled to the frame structure, or independently positioned within the catheter and frame structure. In this way, the elongated member and magnetic elements may be introduced within the catheter and frame structure and thereafter removed (e.g., for continuous replacement during the procedure) while the catheter and/or frame structure remains positioned within the blood vessel.

After the filtering of the therapeutic agent is complete, the catheter may be removed from the blood vessel. In one embodiment, the magnetic filtration device is removed before the catheter. In another embodiment, the catheter is removed from the blood vessel while the magnetic filtration device remains within the catheter. It should also be appreciated that in certain embodiments, the magnetic component is left within the blood vessel while the catheter is removed from the blood vessel. At a later time (e.g., days, weeks, months, etc.) the magnetic element may be removed—e.g., with a snare catheter for instance. It is also appreciated that magnetic elements may be used and/or replaced during the procedure, with a magnetic elements remaining in the blood vessel after the procedure for removal at a later time.

It will be appreciated that in certain embodiments, the therapeutic agent administered to the subject is known to be therapeutically beneficial above a certain concentration level in the blood. After a certain time once the concentration decreases below a specific threshold, it is only primarily toxicity that the patient receives. In such embodiments, the present device may be placed intraarterially or intravenously at the time when the concentration drops below that agent's therapeutic level in order to filter the agent and prevent toxicity. It will be appreciated buy one of skill in the art that this timing may be derivable from published known in vivo kinetics/clearance profile of the therapeutic agent.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Magnetic Filtration Device

Iron oxide nanoparticles when conjugated to chemotherapy agents could play an important role in intra-arterial therapy for head and neck cancers and other tumors. We eventually propose to infuse high doses of iron oxide particles conjugated to chemotherapy agents into a tumor bed and temporarily deploy an intravenous magnetic filter within the vein(s) draining the target organ to capture excess particles thereby decreasing systemic distribution of particles and conjugated chemotherapy agents. This would allow higher local doses of therapy agents to be administered with fewer systemic effects. We demonstrated intravascular magnetic capture of iron oxide nanoparticles in a physiologic flow chamber and in a pig model.

Figure 3:
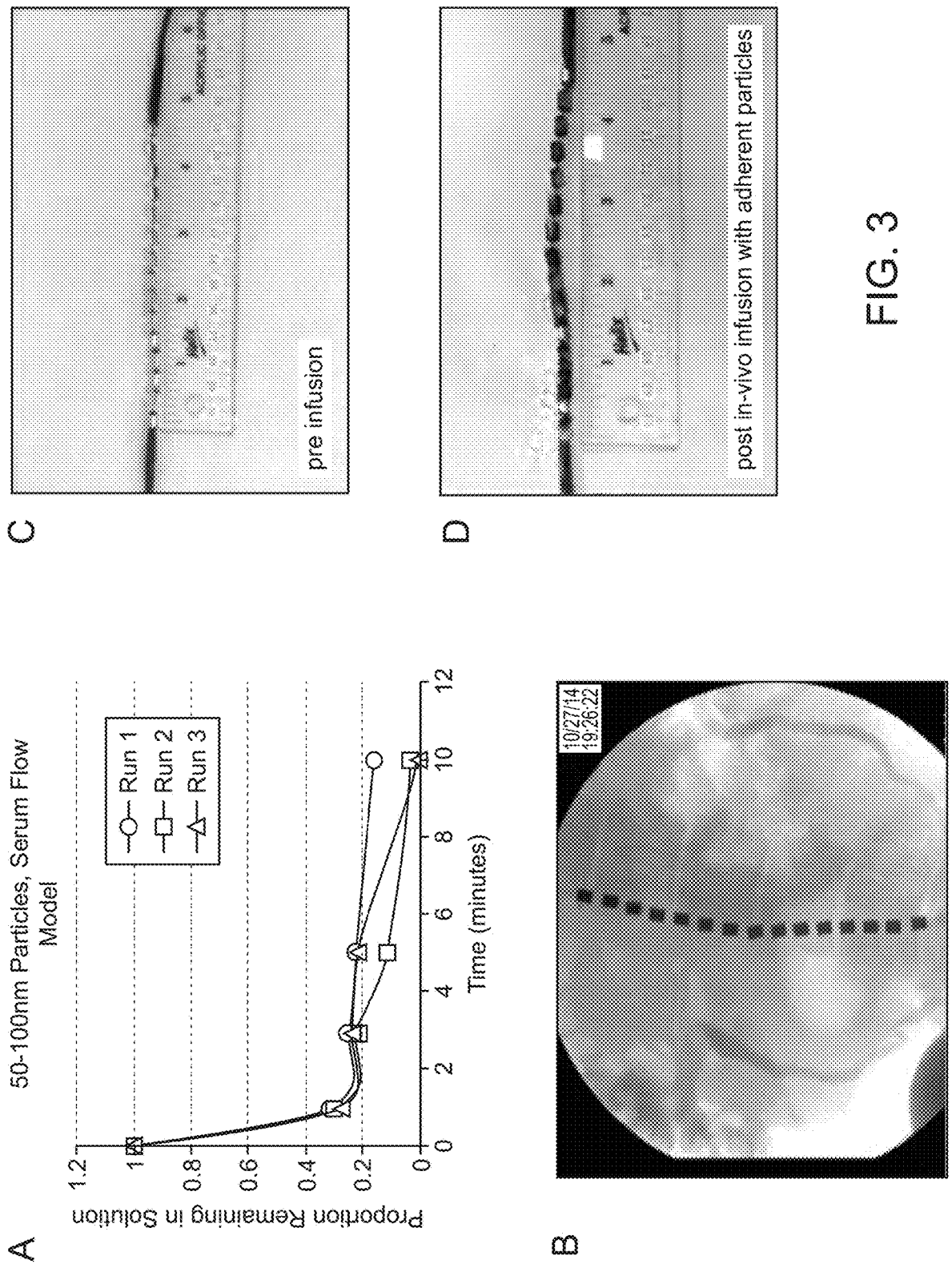
FIG. 3 shows results of use of a magnetic filtration device. Panel A is a graph showing decreasing concentration of iron oxide nanoparticles in a physiologic serum flow model over 10 minutes. Panel B is an image showing the magnetic filtration device positioned in vivo in a pig IVC. Panel C is an image showing the magnetic filtration device pre in vivo infusion. Panel D is an image showing the magnetic filtration device post in vivo infusion and removal with adherent iron oxide nanoparticles.

We developed prototype magnetic filters that we have tested in vitro in both saline solution and porcine serum in a physiologic flow model and have deployed and tested in vivo in the inferior vena cava of a pig. In order to determine whether ferromagnetic particles could be captured magnetically using a small intravascular magnet (simulating capture of particles after passing through a tumor), we constructed a magnetic filter (FIG. 2) composed of toroidal rare earth magnets stacked in alternating polarity into a cylinder similar in diameter to a large endovascular catheter (NdFeB grade N52, K&J Magnetics, Pipersville, Pa.), thus simulating a device that could be placed on the end of a trocar or catheter in the human vena cava. We placed this device in a circulating water bath, in which fluorescent ferrous magnetic microparticles of 5, 12, or 44 micron diameters (Sphero, Spherotech, Lake Forest, Ill.) were suspended. The magnetic filter device rapidly cleared magnetic microparticles from solution, as confirmed by visual identification of particles attached to the device and spectrophotometric concentration measurements of the solution over time. We then moved to a smaller magnet prototype and smaller particles to approximate more clinically realistic conditions. A second smaller wire based prototype device was constructed and demonstrated high uptake of 50-100 nm and 1-5 um iron oxide particles (Sigma-Aldrich, St Louis, Mo.) in a physiologic serum flow model as evidenced by adherent nanoparticles, visual clearing of the solution, and decreasing iron particle concentration over time. We have demonstrated >70% uptake at 1 minute and >90% at 10 minutes in vitro (FIG. 3, Panel A). Feasibility was demonstrated in vivo as evidenced by adherent iron oxide nanoparticles on the magnetic filter following venous infusion (FIG. 3, Panels B-D). The magnetic filter was maneuvered in the venous system without difficult and venography demonstrated a patent inferior vena cava with normal flow around the filter.

The magnetic filter demonstrated efficacy in the physiologic flow model as evidenced by adherent particles, visual clearing of the solution, and decreasing iron particle concentration over time. Mean decrease in concentration for three runs in the flow chamber were 71.6% at 1 minute, 77.0% at 3 minutes, 81.5% at 5 minutes, and 93.8% at 10 minutes. Feasibility was demonstrated in-vivo as evidenced by adherent iron oxide nanoparticles on the magnetic filter following the infusion. The magnetic filter was easily maneuvered in the venous system and venography demonstrated a patent inferior vena cava with normal flow around the filter.

Iron oxide nanoparticles can be effectively removed from serum in-vitro and from flowing venous blood in-vivo by a prototype magnetic filter. This may be combined with conjugated therapeutic agents in the future as an oncologic treatment allowing dose escalation in trans-arterial chemotherapy.

Once fully developed this magnetic filter could work with any magnetic particle (e.g., iron oxide) and bound drug combinations that are developed for use in any venous system in the body. This could potentially be used with thrombolytic therapy (stroke, myocardial infarction, venous/arterial thrombosis or embolus), stem cell therapy (iron oxide particles are used to label stem cells), or any local therapy in which a drug is eventually bound to an iron oxide particle carrier. This could thus be a platform technology for a new paradigm in drug therapy, enabling well-established, low-cost drugs to be used in higher effective doses once bound to iron oxide particles, leading to improved clinical outcomes, less toxicity, and potentially lower overall cost as compared to development and use of new drugs. Given the compelling case for clinical translation of the magnetic filter device and the potential for use in concert with the expanding field of nanoparticle therapeutics, this is an innovative project with significant potential to improve image-guided therapy.

Example 2

Determine Optimal Geometry for Endovascular Magnetic Filtration Devices

Determine optimal geometry for endovascular magnetic filtration devices. Magnetic fields will be modeled for several device configurations with size constraints appropriate for endovascular use. This is based on the hypothesis that the magnet design with the strongest magnetic gradient strength for a given axial dimension will lead to the best capture efficiency.

We have developed initial prototype magnetic filters empirically and constructed them in our laboratory. In order to optimize geometry and construction we will employ magnetic field modeling to predict the magnetic field for theoretical devices based upon the given size constraints of an 18 French diameter (18 Fr) sheath and available permanent magnets.

Figure 4:
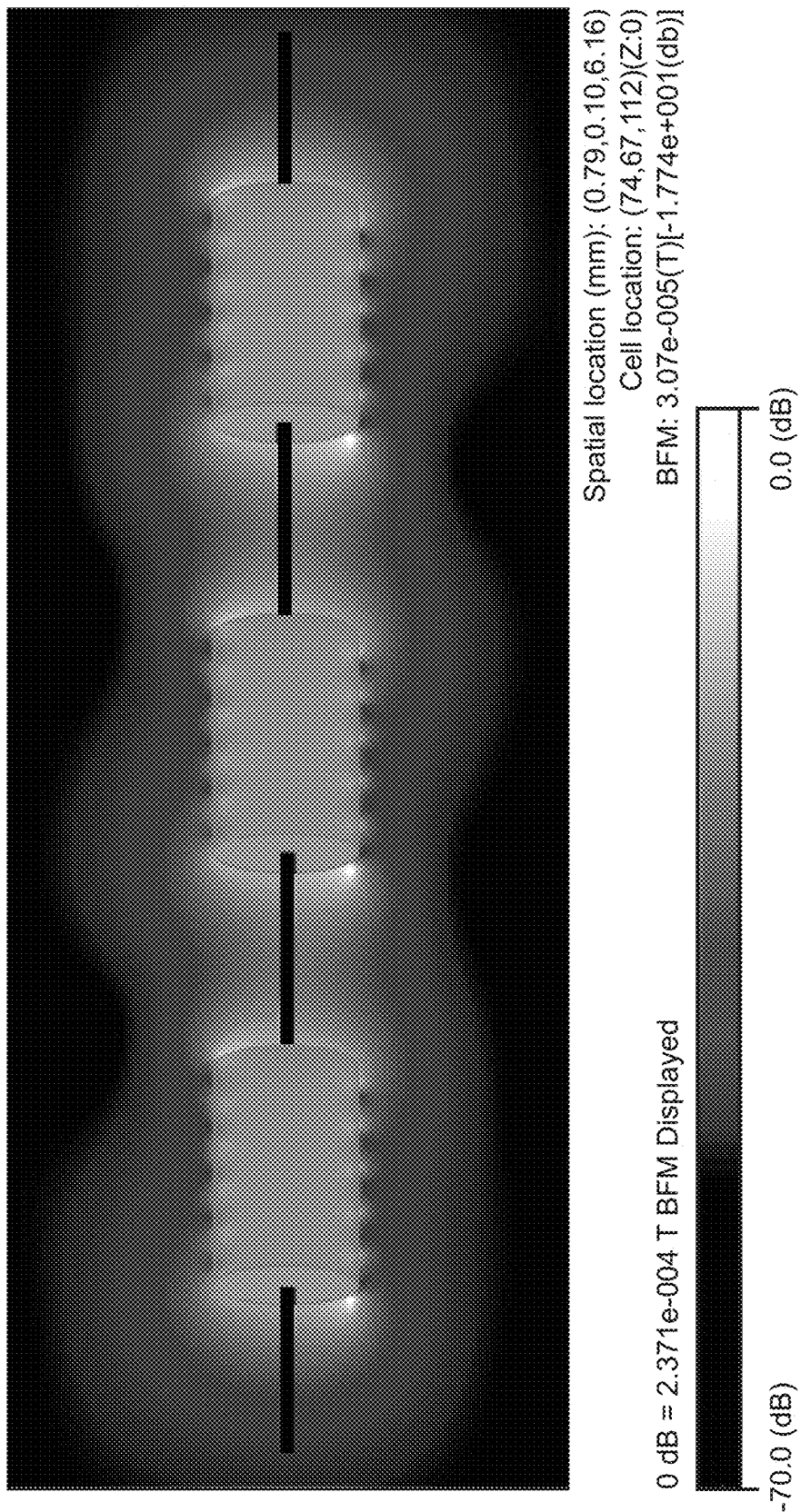
FIG. 4 is an example of an electromagnetic simulation of numerical calculated magnet field map of three cylindrical magnetic dipoles placed in series. Copper-wire solenoid (with a dimension of 3 mm diameter by 6 mm length) fed by a current source were used to mimic cylindrical shaped magnets or magnetic dipoles. With this simulation capability, quantitative evaluation on magnetic field magnitude and spatial distribution can be performed in all three dimensions, for optimizing the magnetic filtration device design.

Electromagnetic modeling and numerical simulation is essential in designing efficient and appropriate magnetic filtration devices to best meet the requirements for the proposed applications. As part of preliminary analysis (shown in FIG. 4), three magnetic dipoles/magnets connected in series were modeled and simulated, showing the magnetic field maps of the structure. The three magnetic dipoles were realized by using copper-wire solenoids fed with currents (magnet dimensions: 3 mm diameter by 6 mm length). The field orientation and magnitude were also obtained in all three dimensions (not shown here). In the proposed project, Comsol multiphysics modeling software (Comsol Inc, Stockholm, Sweden) will be used to model the magnetic fields of potential prototype magnets. We will model two-dimensional and three-dimensional magnetic fields for proposed permanent magnets based upon combinations of the strongest available small commercial magnets. We will assess the effects of magnet orientation (alternating or consistent polarity) and direction of magnetization (lengthwise or axial). Optimized magnet designs will be constructed using commercially available and custom made rare earth magnets (neodymium grade N-52 magnets, SM Magnetics, Pelham, Ala.) and pre-existing wires and catheters. Our strategy in preliminary experiments has been to construct magnets on a wire that fit through an 18 Fr sheath. Several candidate geometries to undergo modeling include multiple short magnets arranged linearly on a wire (as in FIG. 3), magnets arranged in a retractable tulip configuration analogous to clinical IVC filters, and magnets arranged in a retractable double helix configuration. The double helix will place more magnetic elements near the vessel wall than the linear wire design, which places the magnets principally in the central portion of the vessel lumen. The tulip configuration places magnets both in the center of the vessel as well as adjacent to the vessel wall.

We will construct a wire-based magnet based upon the most promising theoretical prototype. Magnetic modeling will help design and develop an optimized magnet given the size and material constraints. Preliminary results have demonstrated that we can empirically construct a magnetic filter on a wire that has demonstrated basic efficacy (i.e., ability to capture magnetic particles in physiologic flow conditions) in vitro and in vivo. The alternative strategy would be further empiric designs based on our current preliminary devices.

Example 3

Computational Optimization of an Endovascular Magnetic Filtration Device for Maximized Capture of Drug-Conjugated Microparticles Endovascular filtration of chemotherapy downstream from intra-arterial infusion according to embodiments described herein minimizes systemic toxicity of therapy and allow for higher-dose therapy. A magnetic filter was introduced to capture chemotherapeutics conjugated to magnetic nano- and microparticles. To further optimize this filter device, a computational simulation of the device in laminar flow to maximize theoretical particle capture was conducted.

Methods

A 3D computational model of the endovascular magnetic chemofilter was created to assess particle capture of different designs with COMSOL Multiphysics software. We simulated series of cylindrical neodymium N52 magnets, centered in a 14 mm-diameter vessel with laminar flow around the device in the vessel. Using this information, we then simulated the release of 1500 particles, each with a 1.0-micron diameter and magnetic properties of iron (II,III) oxide at the inlet of the vessel for each case. The design of the prototype includes three parameters: magnetization orientation, magnet outer diameter, and magnet length. Magnetization orientation varied across the diameter ("D") or along the length ("L") in the following geometeris; outer diameter (3,4,5 mm), single magnet length (5.10 mm); spacing between magnets (1.3 mm). We simulated either 4 magnets with a 5 mm length or 2 magnets with a 10 mm length, and calculated percent capture of the magnetic microparticles.

Results

Device designs with magnetization across the diameter ("D", refer to figure) had higher percent capture than designs with magnetization across the length ("L", refer to figure). Increasing outer diameter of magnets increased particle capture as follows: "D" designs, 3 mm: 12.8-13.6%, 4 mm, 16.6-17.6%, 5 mm: 21.8-22.8%; "L" designs, 3 mm: 5.6-10%, 4 mm: 9.4-15.8%, 5 mm: 18.2-21.2%. While varying magnet length and spacing of "D" designs had minimal effect, particle capture increased with shorter magnets and decreased spacing in "L" designs.

Conclusions

This computational study predicts that endovascular magnetic filters made from permanent N52 magnets demonstrate maximum particle capture when magnetized in the "D" configuration. Additionally, efficacy of magnetic filter prototypes could be improved by using magnets with a larger outer diameter, providing increased magnetic field strength for capture.

Example 4

Validate and Optimize Magnetic Filter Designs In Vitro for Capacity to Capture Iron Oxide Particles We will assess binding capacity of magnetic filtration devices in physiologic flow models including swine serum and iron oxide particles. Optical measurements and magnetometry measurements will assess particle concentration and capture. We hypothesize that filter designs that create the largest local magnetic field strengths over the largest cross-section and length of the simulated vein will demonstrate the largest binding capacity of particles in a physiologic flow model.

Optimized magnetic filters will be assessed in a physiologic flow model with iron oxide particles. We will use the closed circuit in vitro physiologic flow system that we have used in preliminary studies and that has been used in the evaluation of ionic based filters. This system allows rapid throughput analysis of a variety of filter configurations, with measurement of particle concentrations in the solution after an arbitrary time.

Experiments will be performed in the benchtop flow model (flow rate of 750 ml/min to approximate human hepatic/IVC blood flow) to evaluate each design.2 500 mg of iron oxide particles (50-100 nm and 1-5 um) (0.5 mg/mL), will be introduced into the system in 1 L of porcine serum (n=6, 3 for each size particle for each device developed) and allowed to equilibrate over several minutes prior to contact with the magnetic device. 3 mL samples will be taken at 0, 1, 3, 5, and 10 minutes. Control experiments (n=6, 3 with each size particle) will be performed without the filter in the system. Quantification will be via magnetometry (Bartington MS-3, Witney, Enlgand) which may provide quicker, more accurate results than our current colorimetric methods.61 We will assess decrease in concentration as compared to the control curves at each timepoint and compare between devices.

Continuous Flow Alternative

Experiments were performed in a similar continuous flow benchtop flow model with the following changes: 250 mg of iron oxide nanoparticles (50-100 nm) labeled with Zr-89 (100 uCi) will be introduced into a system of 500 mL (0.5 mg/L final concentration, n=3) for each device developed. The system was allowed to equilibrate over several minutes prior to contact with the magnetic device. 3 mL samples were taken at 0, 0.5, 1, 2, 5, and 10 minutes. Control experiments were performed without the filter in the system (n=3, for each device). Secondary control experiments were performed with non-magnetic "D" filter prototypes (containing ring clamps, non-magnetic beads, and rubber spacers) and non-magnetic "L" filter prototypes (ring clamps, non-magnetic beads glued down to constrain spacing), with n=3 for each. Quantification was performed via TLC to assess capture by device, and gamma counting to assess particle concentration in solution.

Figure 11:
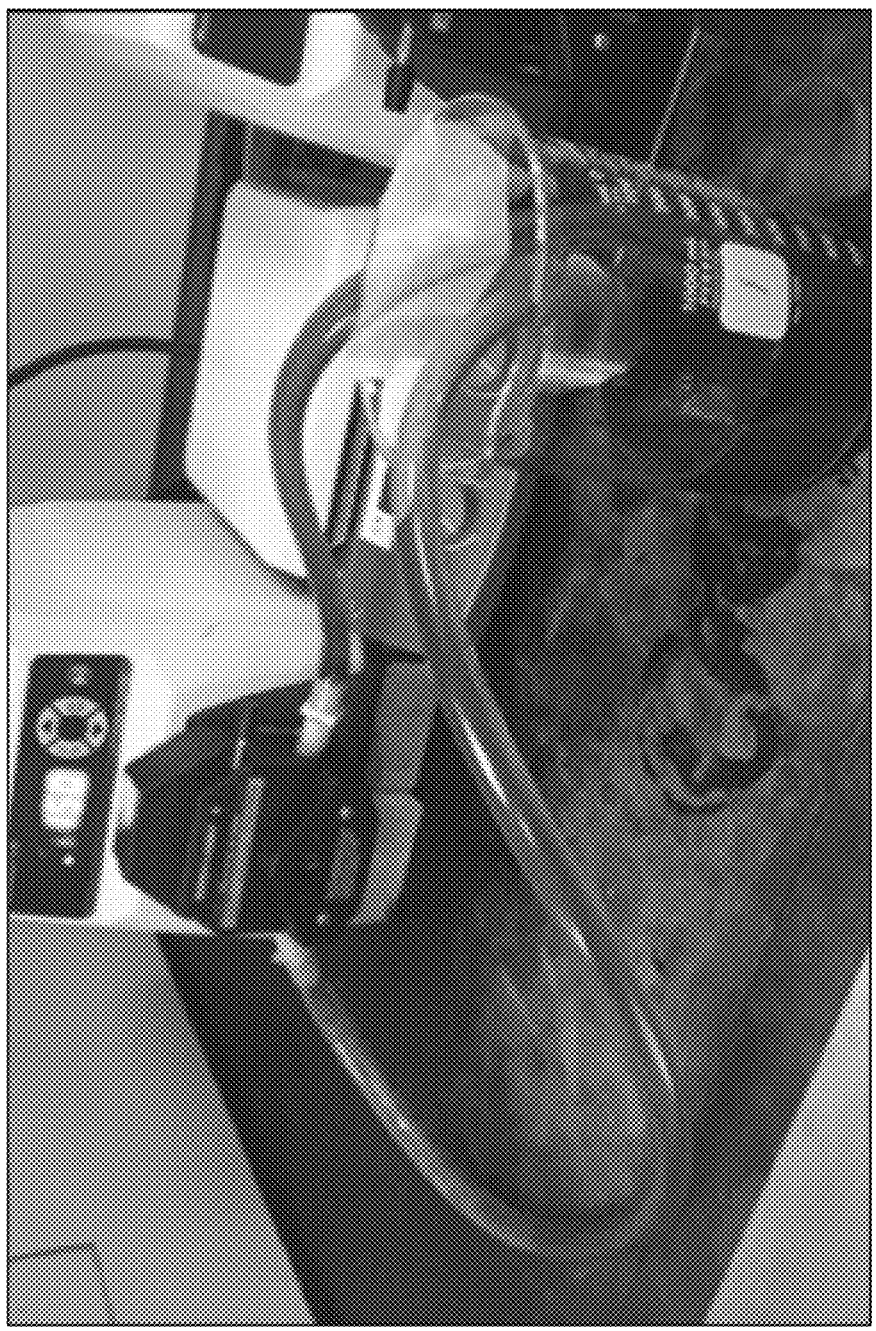
FIG. 11, Panel A depicts a photograph of a continuous flow setup according to certain embodiments.
Figure 11:
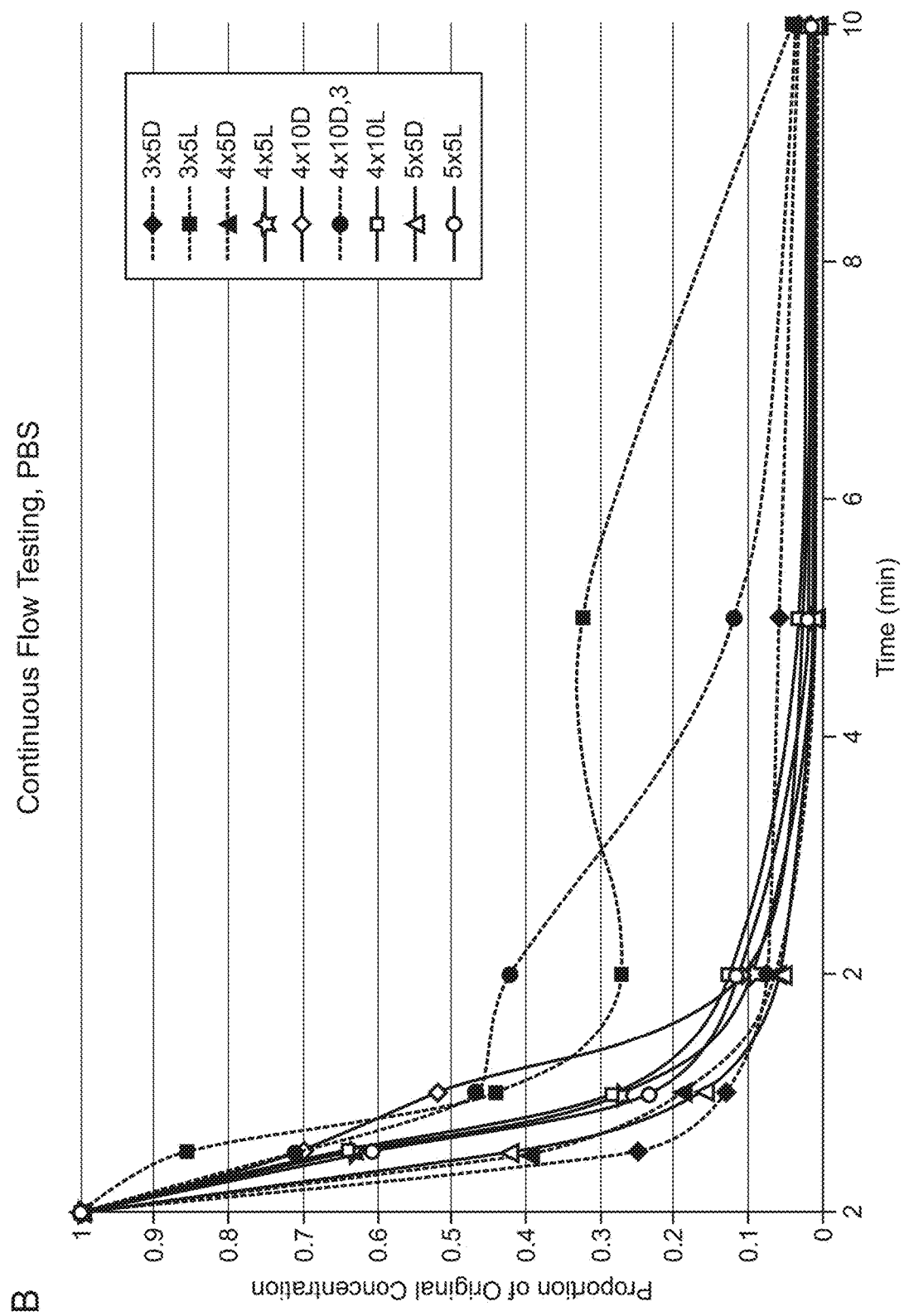

FIG. 11A depicts a photograph of a continuous flow setup according to certain embodiments. FIG. 11B shows the results of the continuous flow setup of PBS with Zr-89 radiolabeled iron oxide particles that are 50-100 nm diameter. Each type of magnetic filtration device is coded by magnetization orientation (L or D), diameter of magnets (mm) and length of magnets (mm)

Single Pass Flow

To assess initial particle capture by a given device, experiments were performed with a single pass flow test setup. The same flow rate, initial concentration of radiolabeled iron oxide nanoparticles, and total starting volume were used. A 3 mL sample (initial concentration) was taken before a single full pass of the solution over the device, from reservoir 1 to reservoir 2, as well as a 3 mL sample after from reservoir 2 (1st pass concentration). Reservoir 2 liquid was then be returned to reservoir 1, flow past the device again, and a 3 mL sample was taken from reservoir 2 (2nd pass). This was repeated and a sample taken again from reservoir 3 (3rd pass). Control experiments were performed with non-magnetic "D" and "L" filter prototypes (n=3, each) as done for the continuous flow experiments. Quantification were performed via TLC to assess capture by device, and gamma counting to assess particle concentration in solution.

Figure 12:
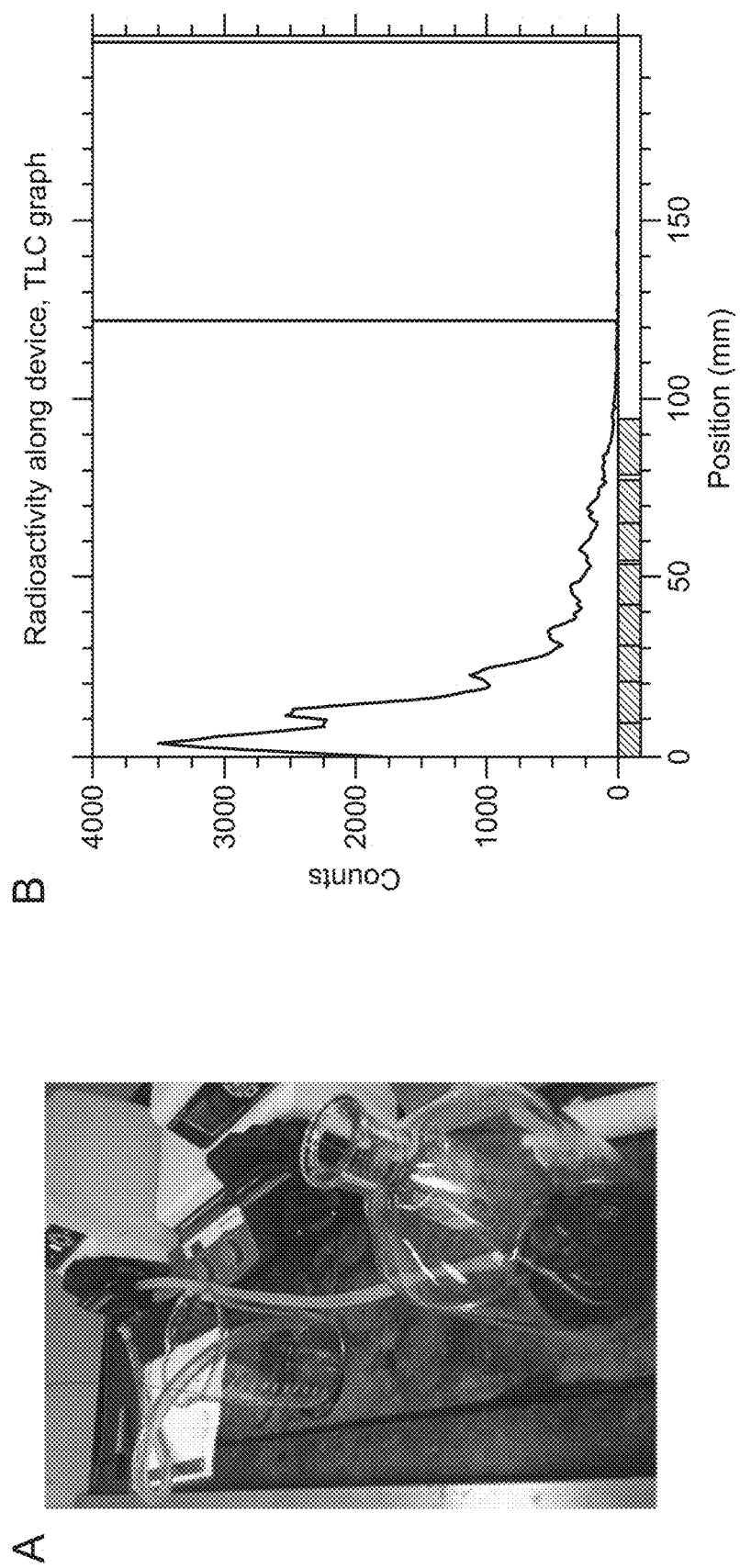
FIG. 12, Panel A depicts a photograph of a single pass flow setup according to certain embodiments.
Figure 12:
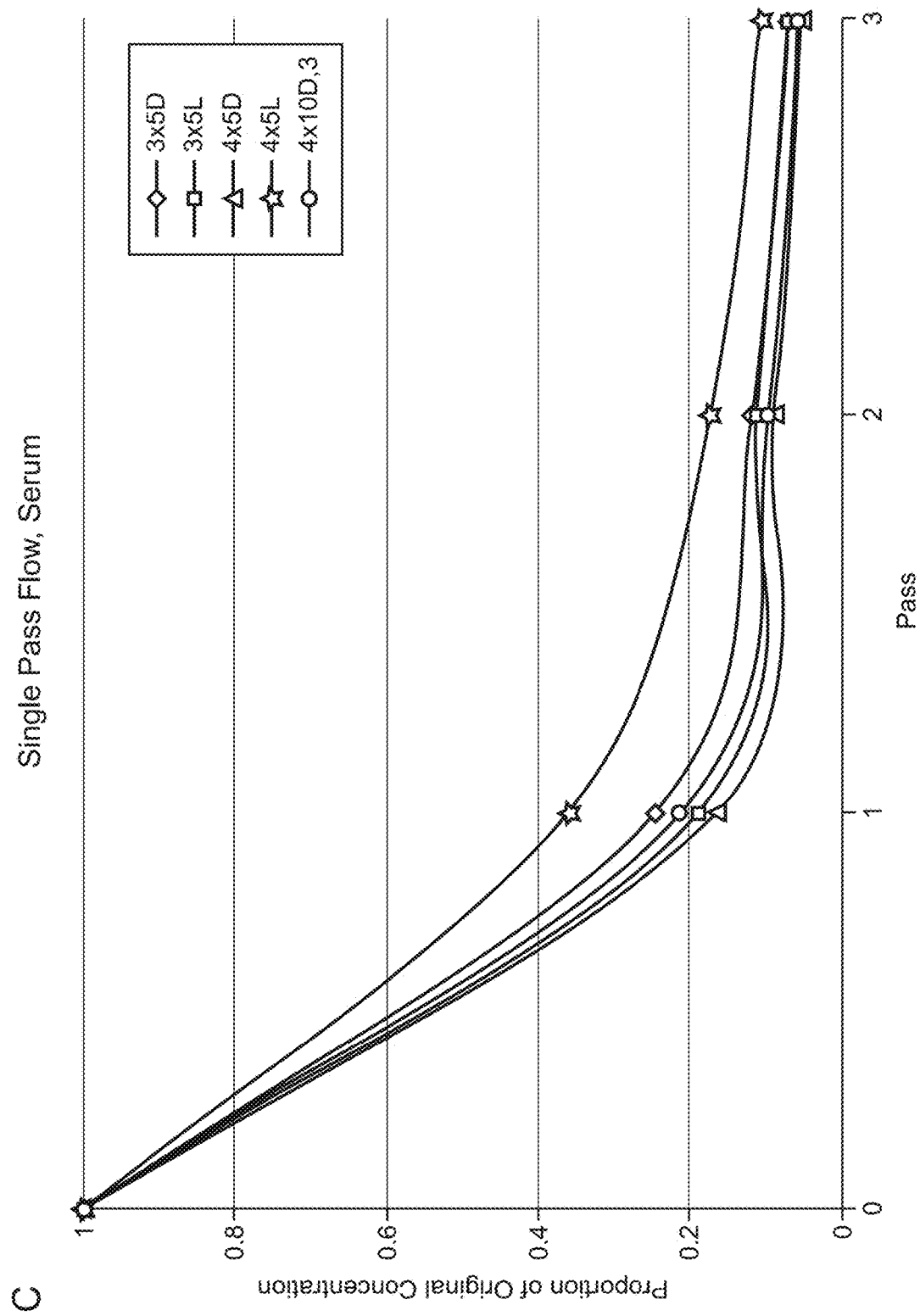

FIG. 12A depicts a photograph of a single pass flow setup according to certain embodiments. FIG. 12B shows a TLC graph with radioactivity along the magnetic filtration device. FIG. 12C shows the results of the single pass flow setup of PBS with Zr-89 radiolabeled iron oxide particles that are 50-100 nm diameter. Each type of magnetic filtration device is coded by magnetization orientation (L or D), diameter of magnets (mm) and length of magnets (mm)

Quantification via radiolabeling allowed for quick processing and accurate evaluation of magnetic nanoparticle uptake. TLC counting enabled detection of radioactive counts along the length of the entire device at the millicurie to microcurie level. Gamma counting enabled detection of radioactivity in both straight PBS and serum samples at the millicurie to picocurie level.

Expected outcomes and alternative strategies: Prototype magnets will be built and will uptake nanometer scale and micrometer scale iron oxide particles in a physiologic flow model. We have demonstrated this ability with our current prototype magnet which will serve as a backup/alternative. Magnetometry will provide faster and simpler readings without overnight processing and is the preferred method. Our current colorimetric method using UV-vis spectrophotometry at 690 nm after digestion in aqua regia and Prussian blue reaction will be an alternative strategy.

Example 5

Evaluate Optimized Magnetic Filter In Vivo for Efficacy and Feasibility to Capture Iron Oxide Particles The most effective devices from in vitro experiments will be tested in the swine inferior vena cava (IVC) under x-ray guidance to assess for feasibility of deployment and resheathing, thrombosis, hemodynamic effects (pressure and flow), and ability to capture infused particles. Serum iron concentrations proximal to the filter, distal to the filter, and remote from the filter will be measured throughout the procedures, and post-procedure MRI and histologic tissue examinations will be performed. We hypothesize that deliverability and resheathability of devices will dictate which designs can be successfully deployed and retrieved in vivo; collateral venous flow will reduce overall efficacy of devices as compared to in vitro experiments but all designs will continue to capture a high fraction of particles in vivo.

Biodistribution of particles was assessed with blood samples taken during infusion experiments from 0-60 minutes, with post-procedure T2* relaxation time and/or quantitative susceptibility mapping from the MRI images, and the standard uptake values (SUV) or the SNR of the PET/MRI images, if the particles are radiolabeled, and postmortem tissue analysis.

Figure 5:
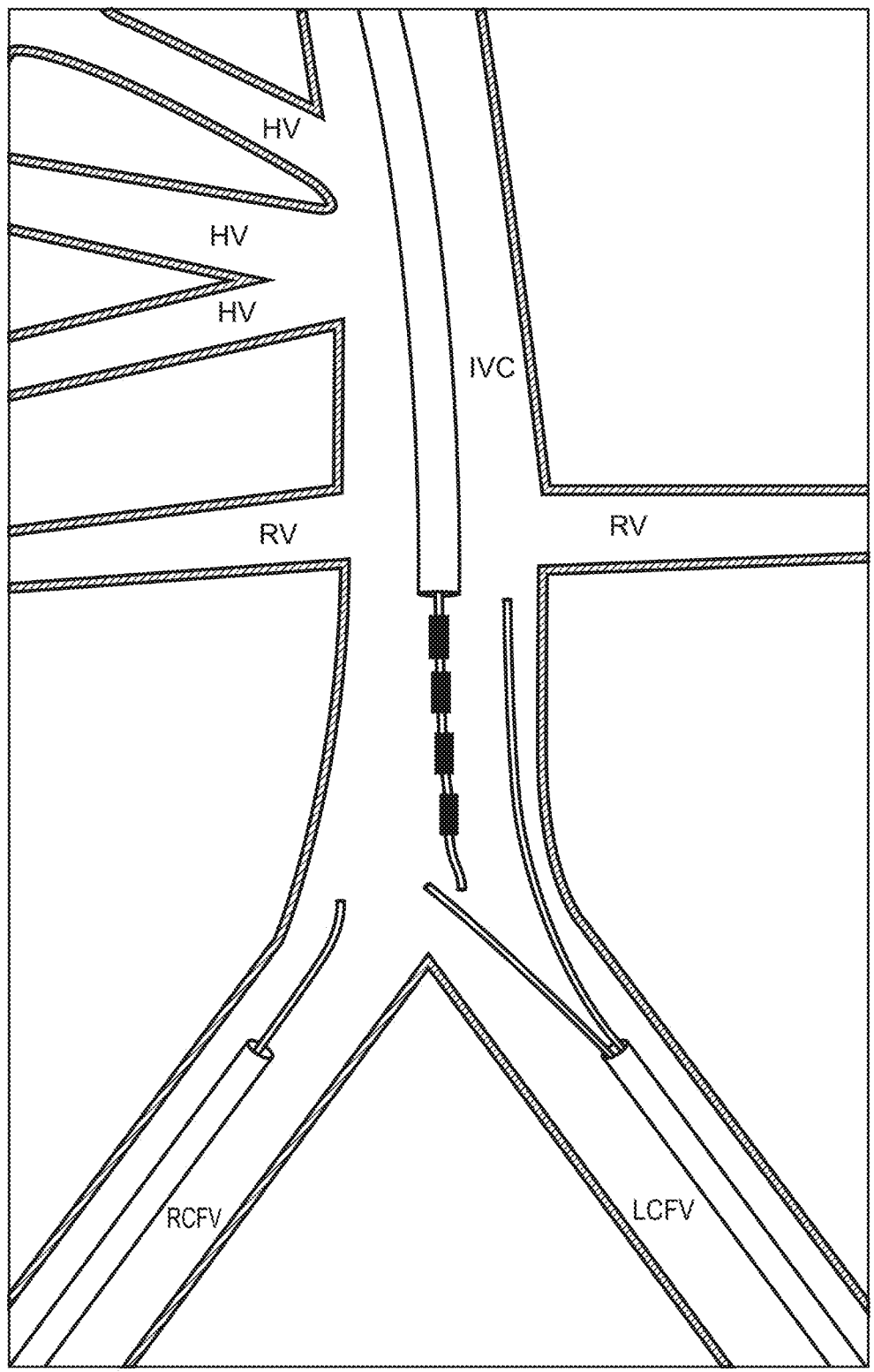
FIG. 5 is an image of an In vivo model for assessment of filter efficacy and biocompatibility. The device is deployed in the infrarenal IVC and sampling catheters are placed above and below it. Test agent can be infused via the sheath in the common femoral artery.

We have established an in vivo model (FIG. 5) to assess the safety, biocompatibility, and agent-capturing efficacy of endovascular filter devices in flowing venous blood without the added variable of organ-specific (e.g., hepatic parenchyma) removal of the test agent between the site of infusion and the site of filtration.1, 2 This model involves x-ray fluoroscopy guided deployment of the device in the infrarenal IVC of the pig. Microcatheters are placed with tips just above and just below the filter to allow for pressure measurements and aspiration of venous blood samples at multiple time points. A site remote from the filter and agent infusion is used to assess systemic levels. The particles are infused through a microcatheter in the iliac vein, mixing with untreated blood from the contralateral iliac vein in the inferior IVC prior to contacting the magnetic filter. Although particles will be infused over 10 minutes, simulating clinical IAC, blood samples and pressure and flow measurements will be taken at various time points up to 60 minutes after infusion in order to assess agent clearance with multiple passes through the filter, release of the agent from the filter over time, and changes in pressure and flow suggestive of device thrombosis. Contrast enhanced x-ray venography will be performed immediately before, after device deployment, and at 60 minutes after device deployment to assess flow and to visualize potential thrombus. The device will then be resheathed and removed. Biodistribution of particles will be assessed with blood samples taken during infusion experiments from 0-60 minutes, with post-procedure T2* MRI, and postmortem tissue sample analysis.41 MRI is being performed to potentially replace tissue sampling in future experiments if we can correlate MRI quantitative signal changes with ferrous particle tissue levels in these experiments. Biocompatibility of the magnetic filter will be assessed by gross inspection for thrombus.

Intravenous particle infusion will be performed on animals with or without (control) the filter device in place in the IVC. Multiple venous pre-filter, venous post-filter, and peripheral venous blood samples will be taken during the procedure to measure blood iron particle concentrations. Post-procedure MRI will be performed to assess tissue iron content. Animals will be euthanized after the final post procedure MRI and post mortem tissue samples will be taken (liver, spleen, kidney, lung, heart, brain). Farm pigs (40-45 kg, n=12) will be purchased from a local vendor and kept in standard animal care facilities. Pigs will be acclimated, fasted, anesthetized, intubated, and euthanized using standard protocols. Animals will undergo continuous $O_2$ saturation, ECG and exhaled $CO_2$ monitoring during all procedures. The following details the procedures for animals in each experimental study group, which are similar to prior chemotherapy filtration animal studies.

Treatment Group (n=6 pigs, venous particle infusion with IVC Magnetic Filter): Access to the femoral veins will be performed with 11 Fr sheaths via Seldinger technique after animals have been prepped and draped in sterile fashion. Heparin (70 IU/kg) will be administered IV hourly during the procedure. Via ultrasound and x-ray fluoroscopic guidance, the magnetic filter device (18 Fr) will be inserted percutaneously through the right femoral or internal jugular vein and will be positioned and deployed in the IVC at least 2 cm inferior to the renal veins. The target agent (500 mg 50-100 nm particles) will be infused via a femoral sheath over approximately 10 minutes. During infusion, blood samples will be obtained from 3 separate sites: IVC pre-filter, IVC post-filter, and peripheral venous (ear vein) at times 0, 1, 3, 5, 10, 12, 15, 30, 45, and 60 min to measure blood particle concentrations. Concentrations will be measured via magnetometry. All catheters including the filter device will be removed. Animals will be taken to MRI and T2* iron quantification MRI will be performed with end organ ROIs (liver, spleen, kidney, bone marrow, brain) to measure T2*/R2*. Animals will recover and be survived for 48 hrs and a 2nd delayed MRI will be performed to assess delayed iron distribution. Animals will be euthanized immediately following the delayed MRI and post mortem tissue samples will be taken. Control Group (n=6 pigs, venous particle infusion without Magnetic Filter): Procedure as described in 'Treatment Group', except no Magnetic Filter device will be placed.

Expected outcomes and alternative strategies: Based on our preliminary data, we hypothesize that compared to control animals undergoing IVC infusion without the Magnetic Filter device the treatment group with magnetic filter in place will have significantly lower iron oxide blood concentrations throughout the 60 minute treatment period and lower end organ iron particle concentrations. We anticipate low mortality and complication rates since dose is within tolerable limits for animal weight and the procedures we propose are similar to clinical endovascular procedures performed frequently by the investigators. The proposed device prototypes seek to optimize magnetic field strength while minimizing impedance of blood flow. Based on our experience with resin-based ionic chemofiltration devices, we expect that systemic heparinization of the experimental animals (a routine clinical practice during many endovascular procedures) will mitigate thrombosis.

The primary endpoints will be blood iron concentrations (magnetometry based, gamma counting based if particles are radiolabeled), end organ T2*/R2* relaxation times or susceptibility values from MRI, PET SUV or SNR in end organs if particles are radiolabeled, device iron concentration (magnetometry based, TLC counting based if particles are radiolabeled), and end organ histological samples (magnetometry). Colorimetric methods for blood, Prussian blue histology for end organs, and ICP-MS for both blood and end organs iron concentrations are established methods that may be used as alternative strategies for iron measurement and to cross-validate magnetometry measurements. MRI measurements will be corroborated with organ tissue samples. Two time points will initially be performed for MRIs, if the initial MRI time point generates detectable signal change and differences between the two groups then the delayed MRI will no longer be performed. If the initial MRI time point does not generate detectable signal change and differenced between the two groups then we will only perform the delayed MRI in the future. If 3T MRI does not prove sensitive enough to assess iron content at either time point, then experiments can be repeated at 7T in the QB3 facility. Iron oxide particles may have a long intravascular half-life (e.g., ferumoxytol has a half-life of 17 hours), however the intravascular half-life of our larger particles has not been established, explaining the initial 2 time points for MRI until the ideal time is established. Based on our preliminary data we expect a standardized effect of at least 1.61. Using alpha 0.05, and power 0.8 yields a needed sample size of 6 for each group using 2-sample t-tests (UCSF CTSI sample size calculator). Two-sample t-tests will be performed between the 2 groups for T2*/R* values for each target organ and tissue concentrations of iron oxide for each target organ. Blood sample curves will be assessed by comparing area under the curves with 2-sample t-tests between control and experimental groups and with 1-way ANOVA between pre, post, and peripheral sample sites within each group.

Achievement of these specific aims will create an optimized magnetic filtration device that could be paired with conjugated magnetic particle-therapeutic agents (e.g., MTC-Dox, SPIO-Dox) to increase the efficacy of locoregional intra-arterial chemotherapy (IAC) by lowering systemic concentrations, thus reducing systemic toxicities, permitting dose escalation in any given IAC procedure and resulting in better local tumor control.

Example 6

Development of an Endovascular Magnetic Filter Device to Enable High Dose Intra-Arterial Chemotherapy: Finite Element Modeling Purpose A temporary endovascular magnetic filter was developed to remove iron oxide particles conjugated to chemotherapeutics from the blood, preventing chemotherapeutics from circulating where it is not needed to reduce systemic toxicity and enable higher dose therapy. Magnetically targeted drug delivery through filtration could play an important role in expanding intra-arterial therapy to head and neck cancer. As described herein, rapid high-capacity binding of iron oxide particles in swine serum in vitro has been established with a preliminary demonstration of efficacy in vivo in a porcine model. As described below, filtration efficacy is demonstrated with finite element magnetic modeling.

Methods

Figure 13:
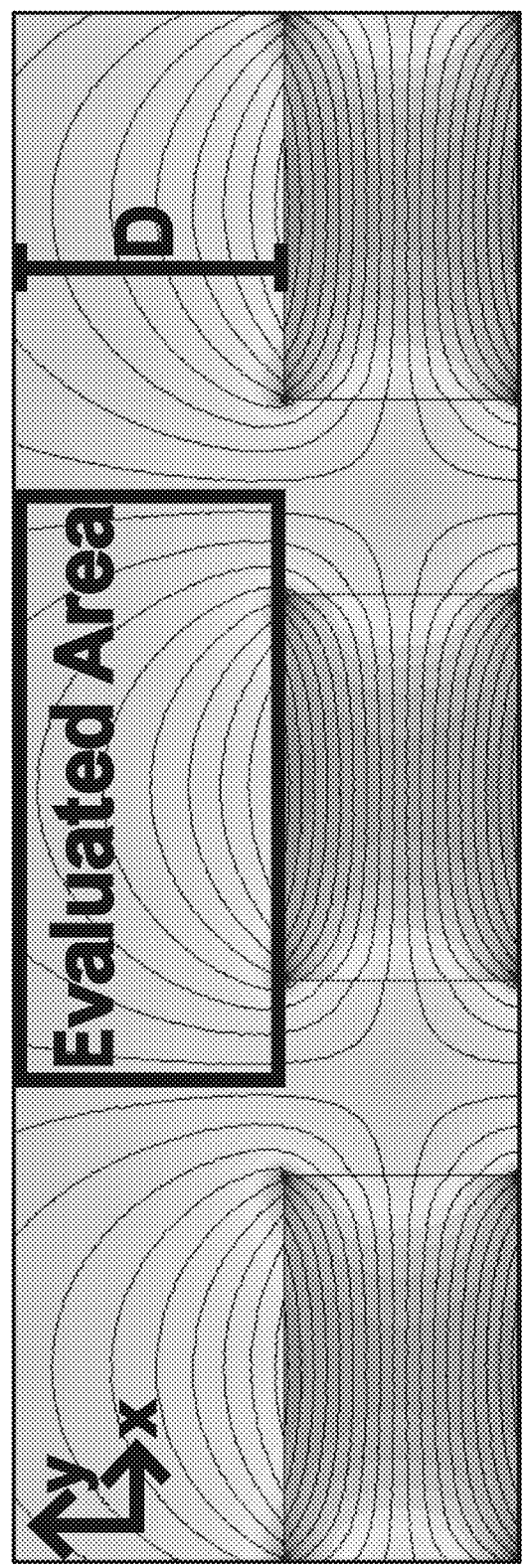
FIG. 13 depicts a diagram of the evaluated area of magnetic flux gradient ($\nabla B_y$) according to certain embodiments.

Magnetic modeling was performed in 2D using Finite Element Method Magnetics (FEMM) software (Brighton, Mass.). Prototype designs consisting of individual neodymium N52 magnets were simulated to optimize the following parameters: i) magnetization across length vs diameter, ii) magnet orientations aligned or reversed, iii) magnet spacing, and iv) magnet length. The average magnetic flux gradient ($\nabla B_y$) was computed across a unit length consisting of one magnet and adjoining gap space as shown in FIG. 13, where r is the vessel radius and D is the distance from the surface of the magnet. $\nabla B_y$ is directly correlated to the magnetic force on an iron particle, and was plotted as against D, distance from the surface of the magnet. Designs with greater $\nabla B_y$ at high D were considered more effective.

Results

Figure 14:
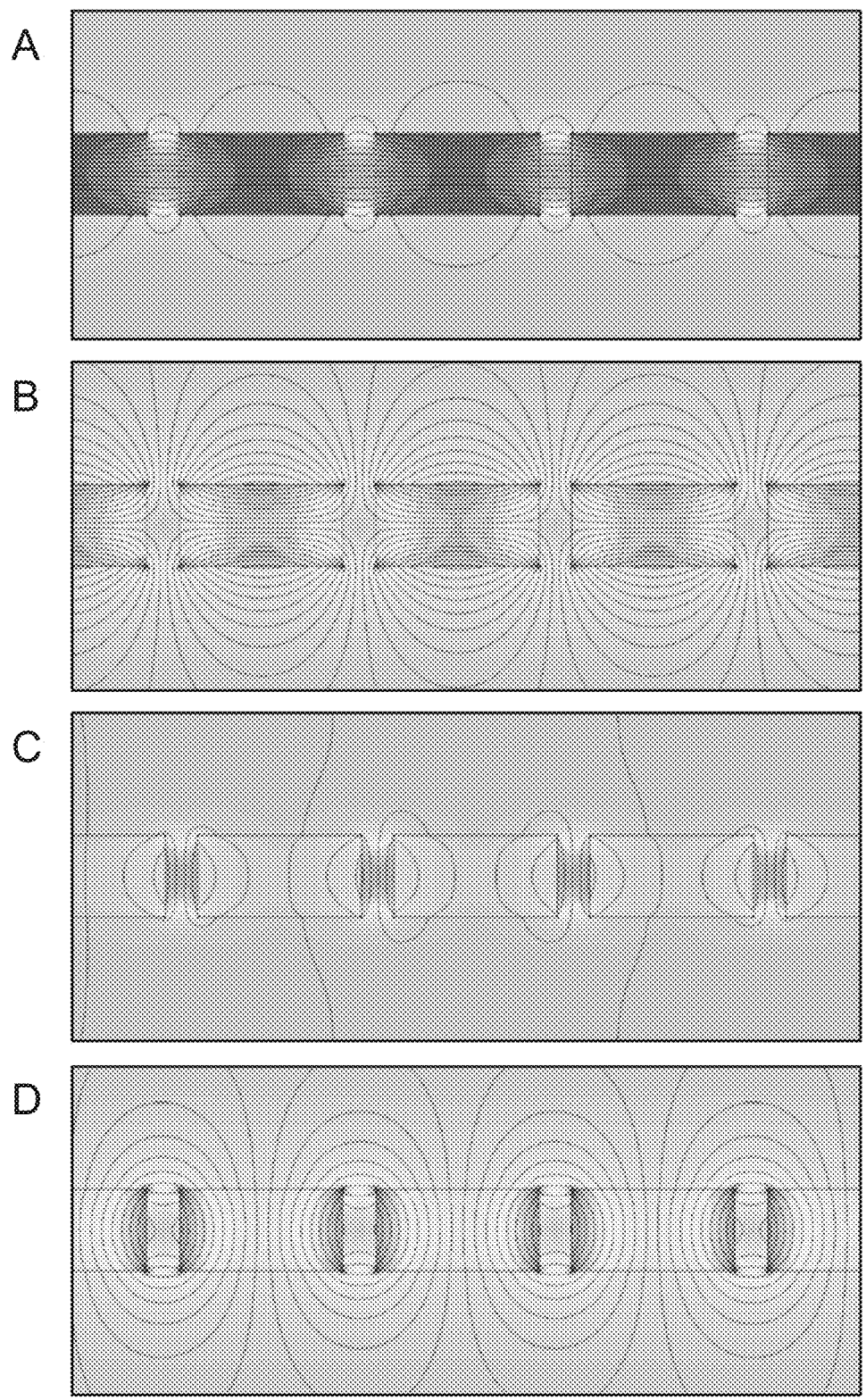
FIG. 14, Panels A-D depicts a magnetic density plot for different orientations of magnets in magnetic filtration devices according to certain embodiments.

FIGS. 14A-14D depicts a magnetic density plot for different orientations of magnets in magnetic filtration devices according to certain embodiments. FIG. 14A depicts magnetic density for a magnetic filtration device having magnets that are arranged where magnetization is across the length and are aligned (LA). FIG. 14B depicts magnetic density for a magnetic filtration device having magnets that are arranged where magnetization is across length and opposed with like polarities together (LO). FIG. 14C depicts magnetic density for a magnetic filtration device having magnets that are arranged where magnetization is across the diameter and aligned (DA). FIG. 14D depicts magnetic density for a magnetic filtration device having magnets that are arranged where magnetization is across the diameter and opposed (DO). Designs with magnetization across the length and reversed (like polarities facing and repelling each other), had slightly higher $\nabla B_y$ than designs with magnetization across the diameter and aligned (opposite polarities facing and attracting each other). (FIGS. 14A-14D) Magnetization across the length and aligned, and magnetization across the diameter and reversed both had low $\nabla B_y$ at high D. For designs with magnetization across the length and reversed orientations as shown in FIGS. 14A-14D, reduced spacing between magnets increased $\nabla B_y$. Reduced magnet length increased $\nabla B_y$ at low D, at the expense of $\nabla B_y$ at high D.

Figure 15:
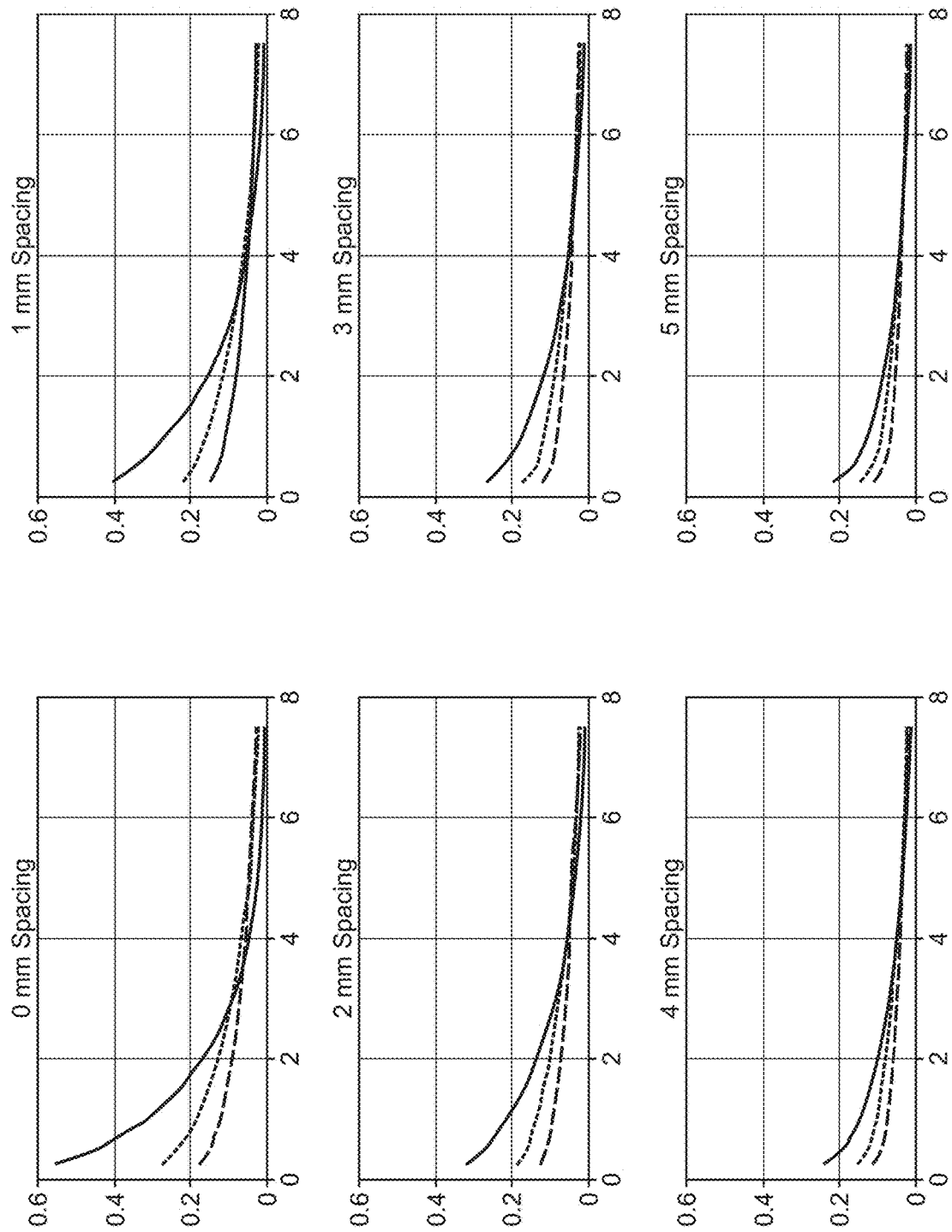
FIG. 15 depicts magnetic flux gradient $\nabla B_y$ (y-axis) vs. distance from magnet (x-axis, mm) for magnets oriented with magnetization across the length and reversed (like polarities facing and repelling each other) with different magnetic lengths according to certain embodiments.

FIG. 15 depicts magnetic flux gradient $\nabla B_y$ (y-axis) vs. distance from magnet (x-axis, mm) for magnets oriented with magnetization across the length and reversed (like polarities facing and repelling each other) with different magnetic lengths, 5 mm, 10 mm and 15 mm. For this orientation, reduced magnet length raised $\nabla B_y$ (y-axis) at the device surface, at the expense of $\nabla B_y$ at the vessel wall.

Figure 16:
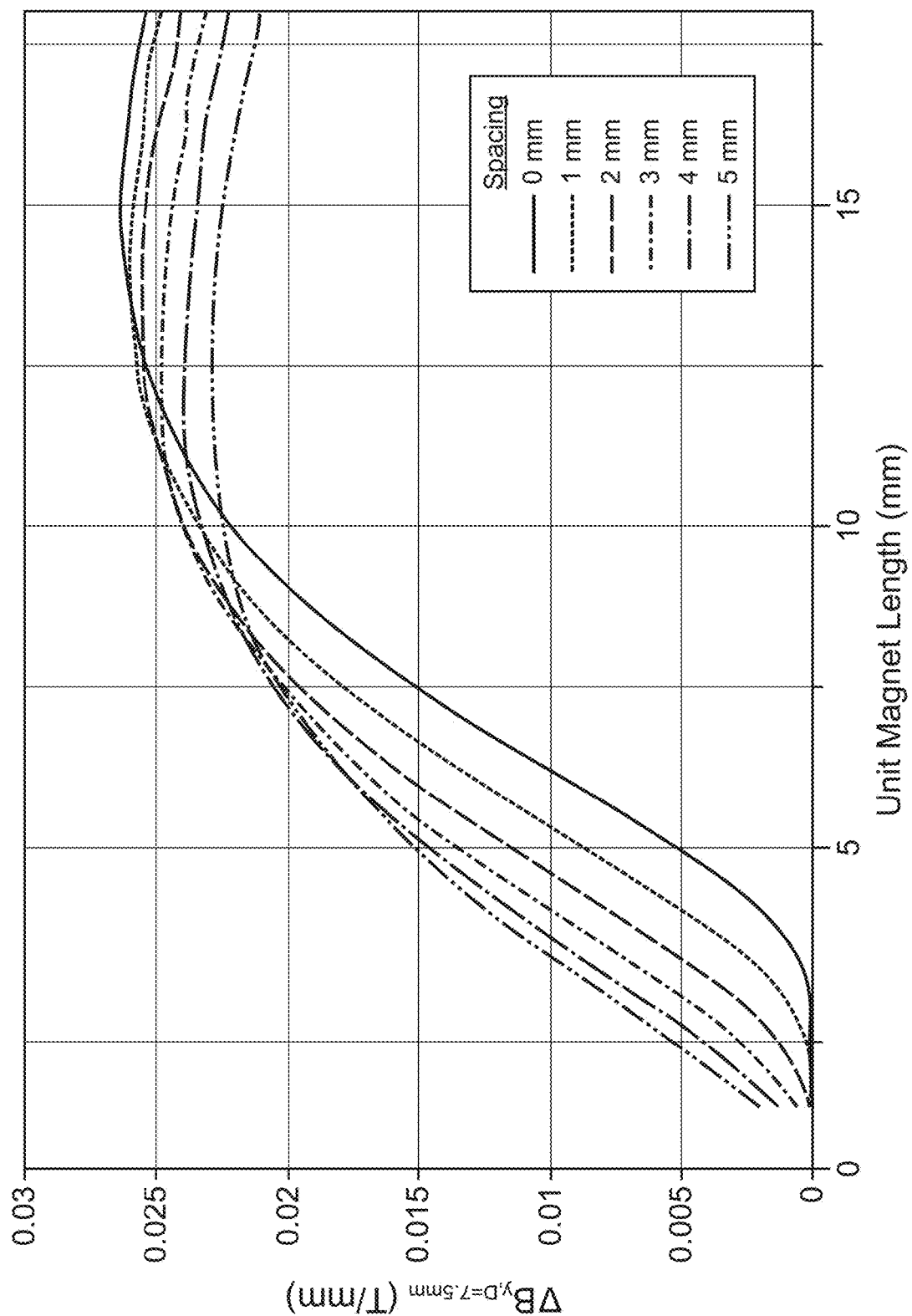
FIG. 16 depicts magnetic flux gradient $\nabla B_y$ at the vessel wall vs. magnet length (x-axis, mm) for magnets oriented with magnetization across the length and reversed (like polarities facing and repelling each other) with different spacing between magnets according to certain embodiments.

FIG. 16 depicts magnetic flux gradient $\nabla B_y$ at the vessel wall vs. magnet length (x-axis, mm) for magnets oriented with magnetization across the length and reversed (like polarities facing an repelling each other) with different spacing between magnets, 0 mm, 1 mm, 2 mm, 3 mm, 4 mm and 5 mm. As demonstrated in FIG. 11, spacing and length can be varied to maximize $\nabla B_y$ at the vessel wall.

Conclusions

Filtration efficacy is demonstrated with finite element magnetic modeling. Longer magnets magnetized across the length in the reversed orientation with like polarities repelling each other and minimal spacing between magnets exhibited strong efficacy in producing suitable magnetic fields for filtration of magnetic particle bound therapeutic agents.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An in vivo positionable magnetic filtration device for filtering one or more therapeutic agents in blood flowing in a blood vessel, the filtration device comprising:
   an elongated member; and a plurality of cylindrical magnetic members concentrically placed along the elongated member with the elongated member positioned in the center of the magnetic members;

wherein the elongated member and the plurality of magnetic members are dimensioned for positioning within a blood vessel of a human or non-human animal; and wherein the plurality of magnetic members comprises a magnetically attractable material to bind a magnetic particle bound to a therapeutic agent from blood.

2. The magnetic filtration device according to claim 1, wherein each magnetic member is spaced apart from each other along the elongated member.

3. The magnetic filtration device according to claim 2, wherein each magnetic member is spaced apart equidistantly along the elongated member.

4. The magnetic filtration device according to claim 2, wherein each magnetic member is spaced apart from each other along the elongated member by 1 mm to 10 mm.

5. The magnetic filtration device according to claim 1, where each magnetic member has a diameter of 3 mm to 5 mm.

6. The magnetic filtration device according to claim 1, where each magnetic member has a length of 5 mm to 10 mm.

7. The magnetic filtration device according to claim 1, further comprising a spacer between each magnetic member.

8. The magnetic filtration device according to claim 7, wherein the spacer is rubber.

9. The magnetic filtration device according to claim 1, wherein the magnetic member comprises permanent magnets.

10. The magnetic filtration device according to claim 9, wherein the magnetic member comprises a toroidal rare earth magnet.

11. The magnetic filtration device according to claim 10, wherein the magnetic member comprises a NdFeB grade N52 neodymium magnet.

12. The magnetic filtration device according to claim 1, wherein the magnetic members are arranged on the elongated member such that magnetization is across the diameter of the magnetic members.

13. The magnetic filtration device according to claim 12, wherein the plurality of magnetic members are oriented in an alternating configuration having the same polarity adjacent to each other.

14. The magnetic filtration device according to claim 1, wherein the magnetic members are arranged on the elongated member such that magnetization is across the length of the magnetic members.

15. The magnetic filtration device according to claim 14, wherein the plurality of magnetic members are oriented in an alternating configuration having the same polarity adjacent to each other.

16. The device according to claim 15, wherein the longitudinal length of each magnetic member is 10 mm or more.

17. The device according to claim 16, wherein the magnetic members are placed adjacent each other along the elongated member without a space separating the magnetic members.

18. A method of in vivo magnetic filtration of a magnetic particle conjugated therapeutic agent, the method comprising:

positioning the magnetic filtration device according to claim 1 in a blood vessel of a body of a human or non-human animal, the filtration device positioned downstream from a target tissue site, the filtration device for magnetically filtering the magnetic particle conjugated therapeutic agent in the blood flowing in the blood vessel; and administering a therapeutic agent conjugated to a magnetic particle upstream from the target tissue site to direct flow of the therapeutic agent to the target tissue site and then to the magnetic filtration device;

wherein the in vivo positioned magnetic filtration device magnetically binds the magnetic particles conjugated to the therapeutic agent as the blood and the therapeutic agent are received by the magnetic filtration device.

19. The method according to claim 18, further comprising:

removing the filtration device from the blood vessel of the body of the human or non-human animal after a completion of the filtering of the therapeutic agent.

20. The method according to claim 19, wherein the positioning of the filtration device comprises:

inserting a catheter within the blood vessel downstream from the target tissue site; and displacing the filtration device at least partially out a distal end of the catheter to position the filtration device downstream from the target tissue site in the blood vessel.

21. The method according to claim 20, wherein the catheter is positioned concentrically around the filtration device when the catheter is inserted within the blood vessel.

22. The method according to claim 18, further comprising:

inserting the filtration device within the catheter after the catheter is inserted within the blood vessel.

23. The method according to claim 18, further comprising:

removing the filtration device from the catheter while the catheter is in the blood vessel, the filtration device removed after filtering the therapeutic agent.

24. The method according to claim 23, further comprising:

inserting a replacement filtration device within the catheter;

displacing the replacement filtration device at least partially out the distal end of the catheter to position the replacement filtration device downstream from the target tissue site in the blood vessel.

25. The method according to claim 18, further comprising:

removing the catheter from the blood vessel and body of the human or non-human animal after a completion of the filtering of the therapeutic agent.

* * * * *